United States Patent [19]
Carlow et al.

[11] Patent Number: 6,150,501
[45] Date of Patent: Nov. 21, 2000

[54] TYROSINE-CONTAINING CYCLOPHILIN AND RELATED METHODS

[75] Inventors: Clotilde K. S. Carlow, Cambridge; Xiqiang Hong, Danvers; Dong Ma, Hamilton, all of Mass.

[73] Assignee: New England Biolabs, Inc., Beverly, Mass.

[21] Appl. No.: 09/028,366

[22] Filed: Feb. 24, 1998

[51] Int. Cl.[7] .................................................. C07K 1/00
[52] U.S. Cl. ........................ 530/350; 530/333; 530/412
[58] Field of Search ................................. 435/69.7, 233; 530/333, 412, 350

[56] References Cited

U.S. PATENT DOCUMENTS

| | | | |
|---|---|---|---|
| 4,722,999 | 2/1988 | Handschumacher et al. | 530/412 |
| 4,885,276 | 12/1989 | Witzel | 514/11 |
| 5,214,130 | 5/1993 | Patchett et al. | 530/333 |
| 5,284,762 | 2/1994 | Hayano et al. | 435/233 |
| 5,324,655 | 6/1994 | Parent et al. | 435/255.2 |
| 5,416,015 | 5/1995 | Hayano et al. | 435/233 |
| 5,447,852 | 9/1995 | Friedman et al. | 435/69.7 |
| 5,480,779 | 1/1996 | Fischer et al. | 435/23 |
| 5,482,850 | 1/1996 | Carlow et al. | 435/233 |
| 5,643,758 | 7/1997 | Guan | 435/69.7 |

FOREIGN PATENT DOCUMENTS

| | | |
|---|---|---|
| 95/11916 | 5/1995 | WIPO . |

OTHER PUBLICATIONS

Ma et al, Molecular and Biochemical Parasitology, vol. 79, 1996, pp. 235–241.
Page et al, Biochemistry, vol. 34, 1995, pp. 11545–11550.
Hong et al, Experimental Parasitology, vol. 88, pp. 246–251, 1998.
Friedman, Cell, 799–806 (1991) vol. 66.
Mikol, Protein Science, 7:1310–1316 (1998).
Borel, Pharamcol. Rev., 41:259:371 (1990).
Luckow, Biotechnology 6:47–55 (1988).
Shine and Dalgarno, PNAS, 71(4);1342–1346 (1974).
Cohen et al, PNAS, 69:2110–2114 (1972).
Chang, et al., Mol. and Gen. Genetics, 168:111–115 (1979).
Parent, et al., Yeast, 1:83–138 (1985).
Shaw, et al., Gene, 23:315 (1983).
Graham and Van Der EB, Virology, 52:456–467 (1973).
Biotechnology, 6:47 (1988).
Denham, Animal Models in Parasitology, ed. D. Owen, 1982, MacMillan, London, pp. 93–104.
Benton & Davis, Science, 196:180–182 (1977).
Sambrook, Molecular Cloning: A Laboratory Manual Cold Spring Harbor Press, 2nd Edition, pp. 17.29–17.33.
Borel, Transplantation Proc. 21:810–815 (1989).
Merck Index, p. 431, 2759 (11th ed., 1989).
Nelson, et al., Journal of Immunology, 150:2139–2147 (1993).
Kallen, et al., Nature, 353:276–279 (1991).
Kallen & Walkinshaw, FEBS Letters, 300:286–290 (1992).
Selzer, et al., Exp. Parasitol., 87:212–221 (1997).
Riberu, et al., Am. J. Trop. Med. Hyg., 43:3–5 (1990).
Grandea, et al., Mol. Biochem. Parasitol., 35:31–41 (1989).
Maina, et al., Gene, 74:365–373 (1988).
Sassenfeld, TIB TECH 8:88–93 (1990).
Bradford, Analytical Biochem., 72:248–254 (1976).
Fischer, et al., Nature 337:476–478 (1989).
Hong, et al., Parasitology, 112:331–338 (1996).
Rosenberg, et al., Gene, 56:125–135 (1987).
Rinfret, et al., Biochemistry, 33:1668–1673 (1994).
Takahashi, et al., Nature, 337:473–475 (1989).
Pflugl, et al., Nature, 361:91–94 (1993).

(List continued on next page.)

*Primary Examiner*—James C. Housel
*Assistant Examiner*—Ginny Allen Portner
*Attorney, Agent, or Firm*—Gregory D. Williams

[57] ABSTRACT

The present invention relates to the use of these cyclophilins, hereinafter referred to as 'tyrosine-containing' cyclophilins, in a method for identifying compounds capable of binding to and/or inhibiting the enzymatic activity of these proteins. Such compounds may be further screened for their ability to inhibit parasites which are not susceptible to the anti-parasitic effects of CsA.

5 Claims, 7 Drawing Sheets

OTHER PUBLICATIONS

Liu, et al., Biochemistry, 30:2305–2310 (1991).
Page, et al., Biochem. J. 317:179–185 (1996).
Blaxter, et al., Mol. Biochem. Parasitol., 77:77–93 (1996).
Chappell, et al., Parasitology, 105 Supplement, S25–S40 (1992).
Bueding, et al., Agents Actions 11:380–383 (1981).
Mack, et al., Antimicrob. Agents Chemother. 26:26–30 (1984).
McCabe, et al., Transplantation, 41:611–615 (1986).
Thommen–Scott, Agents Actions, 11:770–773 (1981).
Hazuda, et al., Drug Des. Discov., 15:17–24 (1997).
Lam, Anticancer Drug Des., 12:145–167 (1997).
Fang, et al., Biochem. Biophys. Res. Commun. 220:53–56 (1996).
Lightowlers, et al., Mol. Biochem. Parasitol., 36:287–289 (1989).
Argaet, et al., J. Parasitol., 78:660–664 (1992).
High, et al., J. Biol. Chem., 269:9105–9112 (1994).
Bell, et al., Biochem. Pharmacol., 48:495–503 (1994).
Reddy, et al., Mol. Biochem. Parasitol., 73:111–121 (1995).
Roberts, et al., Parasitology, 111:591–597 (1995).
Ma, et al., Mol. Biochem. Parasitol., 79:235–241 (1996).
Page, et al., Parasitol. Today, 11:385–388 (1995).
Page, et al., Biochemistry, 34:11545–11550 (1995).
Fischer, et al., Biomed. Biochim. Acta, 43:1101–1111 (1984).
Lang, et al., Nature, 329:268–270 (1987).
Fransson, et al. FEBS Lett., 296:90–94 (1992).
Lodish, et al., J. Bio. Chem., 266:14835–14838 (1991).
Steinmann, et al., J. Biol. Chem., 266:1299–1303 (1991).
Freskgard, et al., Science, 258:466–468 (1992).
Borel, Pharmacol. Rev., 41:259:371 (1990).
Kofron, et al., Biochemistry, 30:6127–6134 (1991).
Handschumacher, et al., Science, 226:544–547 (1984).
Haendler, et al., EMBO J. 6:947–950 (1987).
Koletsky, et al., J. Immunol. 137(3):1054–1059 (1986).
Gething, et al., Nature, 355:33–45 (Jan. 2, 1992).
Price, et al., PNAS, 88:1903–1907 (1991).
Spik, et al., J. Biol. Chem., 266(17),10735–10738 (1991).
Friedman, et al., Cell, 66:p. 799–806 (1991).
Bergsma, et al., J. Biol. Chem., 266:23204–23214 (1991).
Kieffer, et al., J. Biol. Chem., 267:5503–5507 (1992).
Wang, et al., Biochem. J., 314:313–319 (1996).
Anderson, et al., PNAS USA, 90:542–546 (1993).
Klinkert, et al., Mol. Biochem. Parasitol., 75:99–111 (1995).
Kiang, et al., Mol. Biochem., Parasitol. 76:73–82 (1995).

FIG. 1

```
   1 GGTTTAATTACCCAAGTTTGAGACATGGGAAAAAAGCAACACCAGAAGGATAAATTGTATTTGACA   66
   1                         M G K K Q H Q K D K L Y L T                 14
  67 ACCACCGAATGGAAAGAAACTTATGGCGGACATAAAGATAGTACTGGTCGGCGCATACAACGTGCG  132
  15 T T E W K E T Y G G H K D S T G R R I Q R A                          36
 133 TTGTTCAAACGTCTGCCAATTACACATTGCTCTTTATCACTGCTGCCATTTGAGGATCCCGTTTGT  198
  37 L F K R L P I T H C S L S L L P F E D P V C                          58
 199 TCACGAGATGGAATTATTTTTGATTTAACACAAATCATTCCATATCTAAAAAAGCATGGTGTCAAT  264
  59 S R D G I I F D L T Q I I P Y L K K H G V N                          80
 265 CCAGTAACTGGCAAGAAAATGACAGCAAAAGAATTGATTCATTTGAAATTCGATAAAGATGCCGAT  330
  81 P V T G K K M T A K E L I H L K F D K D A D                         102
 331 GGTAATTTTCGATGTCCTGTTACTTTCCGTACTTTCACAGCCACGAGTCATATTGTGGCCATCTGT  396
 103 G N F R C P V T F R T F T A T S H I V A I C                         124
 397 CAAACGGGAAATGTATATTCACTTGAGGCTATCGAAGAATTGAACTTGAAACCCGGACATCTAAGA  462
 125 Q T G N V Y S L E A I E E L N L K P G H L R                         146
 463 GATCTTCTAACCGATGAACCATTTCAGAGGAAGGATATCATTACTTTGCAGGATCCAAATCATTTG  528
 147 D L L T D E P F Q R K D I I T L Q D P N H L                         168
 529 GAAAAATTTAACATTGAGCAATTTCATCATGTAAAACTGGATTTAAAAACAAAGGCTGAAATTGAA  594
 169 E K F N I E Q F H H V K L D L K T K A E I E                         190
 595 GCTGAAAAAAAAGCTATGGAAGATCCAAAATTTCATATCAGATGGATGAATAACGAAACTAAAGAG  660
 191 A E K K A M E D P K F H I R W M N N E T K E                         212
 661 ATTTTAGAAAAACTAGCAAAAGAATATGTCCCAACGAAAATTGAAGAAATAGAAGAAGAAATAACG  726
 213 I L E K L A K E Y V P T K I E E I E E E I T                         234
 727 GATGAACTCAACGCGGCACATTACAGTCAAGGTCGTGTAGCCGCAGGATTAACATCAACAACGATG  792
 235 D E L N A A H Y S Q G R V A A G L T S T T M                         256
 793 GACCCTGTAACACATCAGAAAGCAGCTGCACTTGATGCTGATACCGTCAAATATGCAAGAGTAAAC  858
 257 D P V T H Q K A A A L D A D T V K Y A R V N                         278
 859 AAGAATGGTTATGTAAGGATCCTAACTAATTATGGTGTAATAAATCTTGAATTATTTTGTAAAGAT  924
 279 K N G Y V R I L T N Y G V I N L E L F C K D                         300
 925 GCACCAAGAGCTTGCGGAAACTTCATCAAACATTGTAAAAATGGTTACTACAACAATACCAAGTTC  990
 301 A P R A C G N F I K H C K N G Y Y N N T K F                         322
 991 CATCGAATTATCCGAAATTTTATGATGCAAGGAGGAGATCCGACAGGTACTGGCAAAGGAGGTGAT 1056
 323 H R I I R N F M M Q G G D P T G T G K G G D                         344
1057 TCTATTTGGGGAAAGCCTTTTAAAGATGAATTCAAGTCAACTTTCAGTCATGATCGACGCGGCGTC 1122
 345 S I W G K P F K D E F K S T F S H D R R G V                         366
1123 TTGAGTATGGCAAATCAGGGAACAGATACGAATAAATCGCAATTCTTTATTACTTTTCGATCGTGC 1188
 367 L S M A N Q G T D T N K S Q F F I T F R S C                         388
1189 AGTTATCTGGACGGTAAACATACTATTTTTGGACATGTTGTGGGTGGTACTGGGACACTAAACACT 1254
 389 S Y L D G K H T I F G H V V G G T G T L N T                         410
1255 ATTGAAAAGATAGAAACTGATGAAAGTGGCCGACCAATTGTAGATGTAATTTTTCTTAATGCGGAA 1320
 411 I E K I E T D E S G R P I V D V I F L N A E                         432
1321 ATTTTTGTTGACCCCTTCGAGGAGGCTGAAAAAGCGGTGGAAAAAGAAAGAGAAAATATTCGTTTA 1386
 433 I F V D P F E E A E K A V E K E R E N I R L                         454
1387 GCAAAAACTAATCAAGAAAGTGAAACAATTGCAAATACGCCAGCTACAGCAGTGCAAGTTCCAAAA 1452
 455 A K T N Q E S E T I A N T P A T A V Q V P K                         476
1453 CCGAAGAAATACGGTTTGGGCGTTGGAAAGTACATAAATCTGCCTGAAGTAGTTGCCGCGACAAAG 1518
 477 P K K Y G L G V G K Y I N L P E V V A A T K                         498
1519 CGAACAGCGAACGATATTGCTGAATTTGGCGTACCTAAAAAAACTGCTCACTGCGCAAATCAGATT 1584
 499 R T A N D I A E F G V P K K T A H C A N Q I                         520
1585 TTTGGTGATTTCTCAACTTGGTAAAAAAACTATCTGAGTTGAAACTTCCAAAGAATCCTGAAGACA 1650
 521 F G D F S T W *                                                     542
1585 AAAAAAAACTTCATATCCCATTAAAAAAAAAAAAAAAAAAAAAAAG                      1696
```

FIG. 2

```
(SEQ ID NO: 3) DiCYP-3  MGKKQHQKDKLYLTTTEWKETYGGHKDSTGRRIQRALFKRLPITHCSLSLLPFEDPVCSRDGIIFDLTQIIPYLKKHGVN  80
(SEQ ID NO: 4) CeCYP-4  ----------------S---.SI-----D--T-L---Q------N--------------A-S-E------A-V--------K-  79
(SEQ ID NO: 5) HCYP-60  ---R------M-I-CA-YTHF---K-PD....LPQTN-R---FD------Q--VY---TP---V---LN-V-W---Y-T-  76
(SEQ ID NO: 6) BmCYP-1
(SEQ ID NO: 7) DiCYP-2

DiCYP-3  PVTGKKMTAKELIHLKFDKDADGNFRCPVTFRTFTATSHIVAICQTGNVYSLEAIEELNLKPGHLRDLLTDEPFQRKDII 160
CeCYP-4  -C---PLV--D---------GE--K-----------DH---L--ATS-----H--VQ------N--K-----V--T-A--- 159
HCYP-60  -SN-E-LDGRS--K-N-S-NSE-KYH---L-TV--NNT----VRT-----AY--V-Q--I-AKNF---------S-Q--- 156
BmCYP-1
DiCYP-2

DiCYP-3  TLQDPNHLEKFNIEQFHHVKLDLKTKAEIEAEKKAMEDPKFHIRWMNNETKEILEKLAKEY.....VPTKIEEIEEEITD 235
CeCYP-4  D-----------M---L---------SE--KK--D--K----Y--R---AC-SV-DQ-D---......-K-SSTETD-TA- 234
HCYP-60  -----TN-D---VSN-Y---NNM-IID..PD-E--KQ--SYYLKNT-A--R-T-QE-Y--FKGDEILAATMKAP-KKKV- 234
BmCYP-1
DiCYP-2

DiCYP-3  ELNAAHYSQGRVAAGLTSTTMDPVTHQKAAALDADTVKYARVNKNGYVRIL.TNYGVINLELFCKDAPRACGNFIKHC... 312
CeCYP-4  -I--------K----F---V-A---SN---V--N---R-S--K--AF--LV..--F-PL-----APKV-K--E---T--... 311
HCYP-60  K-------T-K-S-SF---A-V-E-THE---I-E-VLR-QF-K-K----LH.--K-DL----H-DLT-KT-E---RL-... 311
BmCYP-1                                           MS-KD-RRVFLD-T-DGNLA-R-VM---YNDI---T-N--LML-TG  45
DiCYP-2                                           MS-PKVYFDIT-DGS-A-R-VM---ADIV-KTAE--RCL-TG  42

#  ##  #        #                      ###        # #
DiCYP-3  .........KNGYYNNTKFHRIIRNFMMQGGDPT.GTGKGGDSIWGKPFKDEFKSTFSHDRRGVLSMANQGTDTNKSQFF 382
CeCYP-4  .........S-------------K---L-------.---H------D---S---I-G----A---------K-SN--G---- 381
HCYP-60  .........-KH--DG-I---S----VI------.---T--E-Y---------RPNL--TG--I-----S-PNS-R---- 381
BmCYP-1  MAGTGKISG-PLH-KGST----V-K---I-----F-K-D-T--E--Y-GM-D--.EFVMK--EPF-V----K-PN--G---- 124
DiCYP-2  ERGVGR.SG-KLH-KGS----V-P---L-----F-R-N-T--E--Y-EK-P--.NFQEK-TGP--------A-PN--G---- 120

#
DiCYP-3  ITFRSCSYLDGKHTIFGHVVGGTGTLNTIEKIETDE.SGRPIVDVIFLNAEIFVDPFEEAEKAVEKERENIRLAKTNQES 461
CeCYP-4  ----P-K---R------RL---QD--T----L--E-GTDV-M-S-VIMR--V----------EVQA--AE-.-K--SKDA 460
HCYP-60  ------A---K-------R----FDV-TAM-NV-S-PKTD--KEEIRIDATTV----Y---DAQIAQ--K....TQLKVAP 457
BmCYP-1  --TTPAPH-NNI-VV--K--S-QEVVTK--YLK-NS.KN--LA--VI--CGEL-RRKKRQHSSRSN-SVSSSTSTEKSHK 203
DiCYP-2  -CTAKTEW------VV--R--E-MNVVKA--.SKGSQ.---TSA--VITDCGQL*                          171

DiCYP-3  ETIANTPATAVQVPKPKKYGLGVGKYINLPEVVAATKRTANDIAEFGVPKKTAHCANQIFGDFSTW*              527
CeCYP-4  ASL--KK-KET.AT--EA--T-----MKSAAA-NKRQGKME-V.PLEAA---KF.-RAGL----K-*              523
HCYP-60  --KVKSSQPQAGSQG-QTFRQ-------PAATKR-AEEEPSTS-TVPMS--K...PSRG-----S-*              520
BmCYP-1  K-KKTKMKEKKRKESDEVEQ-EI-TVVPEA-LQLSSVKAEDLPD-PDHQN-YLMRRSKTPENSRKG>              269
DiCYP-2
```

A: LAMBDA DNA-BstII DIGESTS

B: ΦX174 DNA-HaeIII DIGEST

C: D.immitis (PLASMID)

D: O.vovulus (cDNA LIBRARY STOCK)

E: O.vovulus (cDNA LIBRARY STOCK)

F: B.malayi (cDNA LIBRARY STOCK)

G: B.malayi (cDNA LIBRARY STOCK)

FIG. 4

A comparison of O.volvulus PCR fragment and DiCyp-3 sequences

```
(SEQ ID NO: 8)   1 ....................atttaacacaaatcattcnntatctaaaaa  30
                                      ||||||||||||||||||::|||||||||||
(SEQ ID NO: 9) 201 ACGAGATGGAATTATTTTTGATTTAACACAAATCATTCCATATCTAAAAA 250

31 agnntggttttnaatccagtaactggcaagaaaatnacngcaaaagaattg  80
                   ||::||||  |:||||||||||||||||||||||:||:||||||||||||
               251 AGCATGGTGTCAATCCAGTAACTGGCAAGAAAATGACAGCAAAAGAATTG 300

81 attcntttnaaatncnntaaagatnccgatggtaatttncnntntcntct 130
                   ||||:|||:||||:|::||||||:|||||||||||:|:::|:||:| |
               301 ATTCATTTGAAATTCGATAAAGATGCCGATGGTAATTTTCGATGTCCTGT 350

131 tactttcc..actttcacagcnacagncatatgtgca............. 165
                   ||||||||  ||||||||||:||  :       ||
               351 TACTTTCCGTACTTTCACAGCCACGAGTCATATTGTGGCCATCTGTCAAA 400
```

A: PROTEIN MARKER, BROAD RANGE

B: UNCUT MBP-DiCYP3e FUSION

C: MBP-DiCYP3e FUSION CUT WITH FACTOR Xa

D: PURIFIED DiCYP3e

FIG. 7

Substrate specificity of filarial cyclophilins toward various peptide substrates $k_{cat}/K_m$ (mM$^{-1}$s$^{-1}$) (relative rate)

| Ala-Xaa-Pro-Phe | DiCYP-3 | BmCYP-1 | BmCYP-2 |
|---|---|---|---|
| -Ala- | 392± 42(1.00) | 1,614± 14(1.00) | 3,906± 43(1.00) |
| -Glu- | 58± 34(0.15) | 61± 25(0.04) | 1,674±644(0.43) |
| -Phe- | 70± 25(0.18) | 19± 2(0.01) | 95± 26(0.02) |
| -His- | 36± 7(0.09) | 19± 1(0.01) | 112± 2(0.03) |
| -Ile- | 313± 54(0.80) | 172± 16(0.11) | 404± 9(0.10) |
| -Lys- | 133± 28(0.34) | 65± 4(0.04) | 242± 26(0.06) |
| -Leu | 392± 50(1.00) | 179± 15(0.11) | 363± 35(0.09) |
| -Nle- | 825±108(2.10) | 252± 45(0.16) | 518± 35(0.13) |
| -Gln- | 233± 58(0.59) | 229±129(0.14) | 414±138(0.11) |
| -Val- | 343± 63(0.88) | 254± 50(0.16) | 569± 60(0.15) |
| -Trp- | 14± 2(0.04) | 12± 3(0.01) | 52± 9(0.01) |
| *-Phe- | 8± 2(0.02) | 19± 3(0.01) | 52± 15(0.01) |

The Xaa is shown in the first column (Nle is the artificial amino acid norleucine). Asterisk denotes tripeptide substrate Suc-F-P-F-pNA. First-order rate kinetics were calculated using the formula: $k_{obs} = (k_{cat}/K_m)[E]$.

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 1696 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 25...1603
        (D) OTHER INFORMATION:

(xi) SEQUENCE DESCRIPTION: SEQ ID NO:1:

```
GGTTTAATTA CCCAAGTTTG AGAC ATG GGA AAA AAG CAA CAC CAG AAG GAT        51
                          Met Gly Lys Lys Gln His Gln Lys Asp
                           1               5

AAA TTG TAT TTG ACA ACC ACC GAA TGG AAA GAA ACT TAT GGC GGA CAT        99
Lys Leu Tyr Leu Thr Thr Thr Glu Trp Lys Glu Thr Tyr Gly Gly His
 10              15                  20                  25

AAA GAT AGT ACT GGT CGG CGC ATA CAA CGT GCG TTG TTC AAA CGT CTG       147
Lys Asp Ser Thr Gly Arg Arg Ile Gln Arg Ala Leu Phe Lys Arg Leu
                 30                  35                  40

CCA ATT ACA CAT TGC TCT TTA TCA CTG CTG CCA TTT GAG GAT CCC GTT       195
Pro Ile Thr His Cys Ser Leu Ser Leu Leu Pro Phe Glu Asp Pro Val
             45                  50                  55

TGT TCA CGA GAT GGA ATT ATT TTT GAT TTA ACA CAA ATC ATT CCA TAT       243
Cys Ser Arg Asp Gly Ile Ile Phe Asp Leu Thr Gln Ile Ile Pro Tyr
         60                  65                  70

CTA AAA AAG CAT GGT GTC AAT CCA GTA ACT GGC AAG AAA ATG ACA GCA       291
Leu Lys Lys His Gly Val Asn Pro Val Thr Gly Lys Lys Met Thr Ala
 75                  80                  85

AAA GAA TTG ATT CAT TTG AAA TTC GAT AAA GAT GCC GAT GGT AAT TTT       339
Lys Glu Leu Ile His Leu Lys Phe Asp Lys Asp Ala Asp Gly Asn Phe
 90              95                 100                 105

CGA TGT CCT GTT ACT TTC CGT ACT TTC ACA GCC ACG AGT CAT ATT GTG       387
Arg Cys Pro Val Thr Phe Arg Thr Phe Thr Ala Thr Ser His Ile Val
                110                 115                 120

GCC ATC TGT CAA ACG GGA AAT GTA TAT TCA CTT GAG GCT ATC GAA GAA       435
Ala Ile Cys Gln Thr Gly Asn Val Tyr Ser Leu Glu Ala Ile Glu Glu
            125                 130                 135

TTG AAC TTG AAA CCC GGA CAT CTA AGA GAT CTT CTA ACC GAT GAA CCA       483
Leu Asn Leu Lys Pro Gly His Leu Arg Asp Leu Leu Thr Asp Glu Pro
        140                 145                 150

TTT CAG AGG AAG GAT ATC ATT ACT TTG CAG GAT CCA AAT CAT TTG GAA       531
Phe Gln Arg Lys Asp Ile Ile Thr Leu Gln Asp Pro Asn His Leu Glu
    155                 160                 165
```

-continued

```
AAA TTT AAC ATT GAG CAA TTT CAT CAT GTA AAA CTG GAT TTA AAA ACA      579
Lys Phe Asn Ile Glu Gln Phe His His Val Lys Leu Asp Leu Lys Thr
170             175                 180                 185

AAG GCT GAA ATT GAA GCT GAA AAA AAA GCT ATG GAA GAT CCA AAA TTT      627
Lys Ala Glu Ile Glu Ala Glu Lys Lys Ala Met Glu Asp Pro Lys Phe
                190                 195                 200

CAT ATC AGA TGG ATG AAT AAC GAA ACT AAA GAG ATT TTA GAA AAA CTA      675
His Ile Arg Trp Met Asn Asn Glu Thr Lys Glu Ile Leu Glu Lys Leu
                    205                 210                 215

GCA AAA GAA TAT GTC CCA ACG AAA ATT GAA GAA ATA GAA GAA GAA ATA      723
Ala Lys Glu Tyr Val Pro Thr Lys Ile Glu Glu Ile Glu Glu Glu Ile
                        220                 225                 230

ACG GAT GAA CTC AAC GCG GCA CAT TAC AGT CAA GGT CGT GTA GCC GCA      771
Thr Asp Glu Leu Asn Ala Ala His Tyr Ser Gln Gly Arg Val Ala Ala
            235                 240                 245

GGA TTA ACA TCA ACA ACG ATG GAC CCT GTA ACA CAT CAG AAA GCA GCT      819
Gly Leu Thr Ser Thr Thr Met Asp Pro Val Thr His Gln Lys Ala Ala
250                 255                 260                 265

GCA CTT GAT GCT GAT ACC GTC AAA TAT GCA AGA GTA AAC AAG AAT GGT      867
Ala Leu Asp Ala Asp Thr Val Lys Tyr Ala Arg Val Asn Lys Asn Gly
                270                 275                 280

TAT GTA AGG ATC CTA ACT AAT TAT GGT GTA ATA AAT CTT GAA TTA TTT      915
Tyr Val Arg Ile Leu Thr Asn Tyr Gly Val Ile Asn Leu Glu Leu Phe
                    285                 290                 295

TGT AAA GAT GCA CCA AGA GCT TGC GGA AAC TTC ATC AAA CAT TGT AAA      963
Cys Lys Asp Ala Pro Arg Ala Cys Gly Asn Phe Ile Lys His Cys Lys
                        300                 305                 310

AAT GGT TAC TAC AAC AAT ACC AAG TTC CAT CGA ATT ATC CGA AAT TTT     1011
Asn Gly Tyr Tyr Asn Asn Thr Lys Phe His Arg Ile Ile Arg Asn Phe
315                 320                 325

ATG ATG CAA GGA GGA GAT CCG ACA GGT ACT GGC AAA GGA GGT GAT TCT     1059
Met Met Gln Gly Gly Asp Pro Thr Gly Thr Gly Lys Gly Gly Asp Ser
330                 335                 340                 345

ATT TGG GGA AAG CCT TTT AAA GAT GAA TTC AAG TCA ACT TTC AGT CAT     1107
Ile Trp Gly Lys Pro Phe Lys Asp Glu Phe Lys Ser Thr Phe Ser His
                350                 355                 360

GAT CGA CGC GGC GTC TTG AGT ATG GCA AAT CAG GGA ACA GAT ACG AAT     1155
Asp Arg Arg Gly Val Leu Ser Met Ala Asn Gln Gly Thr Asp Thr Asn
                    365                 370                 375

AAA TCG CAA TTC TTT ATT ACT TTT CGA TCG TGC AGT TAT CTG GAC GGT     1203
Lys Ser Gln Phe Phe Ile Thr Phe Arg Ser Cys Ser Tyr Leu Asp Gly
                        380                 385                 390

AAA CAT ACT ATT TTT GGA CAT GTT GTG GGT GGT ACT GGG ACA CTA AAC     1251
Lys His Thr Ile Phe Gly His Val Val Gly Gly Thr Gly Thr Leu Asn
395                 400                 405

ACT ATT GAA AAG ATA GAA ACT GAT GAA AGT GGC CGA CCA ATT GTA GAT     1299
Thr Ile Glu Lys Ile Glu Thr Asp Glu Ser Gly Arg Pro Ile Val Asp
410                 415                 420                 425

GTA ATT TTT CTT AAT GCG GAA ATT TTT GTT GAC CCC TTC GAG GAG GCT     1347
Val Ile Phe Leu Asn Ala Glu Ile Phe Val Asp Pro Phe Glu Glu Ala
                430                 435                 440

GAA AAA GCG GTG GAA AAA GAA AGA GAA AAT ATT CGT TTA GCA AAA ACT     1395
Glu Lys Ala Val Glu Lys Glu Arg Glu Asn Ile Arg Leu Ala Lys Thr
                    445                 450                 455

AAT CAA GAA AGT GAA ACA ATT GCA AAT ACG CCA GCT ACA GCA GTG CAA     1443
Asn Gln Glu Ser Glu Thr Ile Ala Asn Thr Pro Ala Thr Ala Val Gln
                        460                 465                 470

GTT CCA AAA CCG AAG AAA TAC GGT TTG GGC GTT GGA AAG TAC ATA AAT     1491
Val Pro Lys Pro Lys Lys Tyr Gly Leu Gly Val Gly Lys Tyr Ile Asn
```

```
          475                 480                 485
CTG CCT GAA GTA GTT GCC GCG ACA AAG CGA ACA GCG AAC GAT ATT GCT    1539
Leu Pro Glu Val Val Ala Ala Thr Lys Arg Thr Ala Asn Asp Ile Ala
490                 495                 500                 505

GAA TTT GGC GTA CCT AAA AAA ACT GCT CAC TGC GCA AAT CAG ATT TTT    1587
Glu Phe Gly Val Pro Lys Lys Thr Ala His Cys Ala Asn Gln Ile Phe
                510                 515                 520

GGT GAT TTC TCA ACT T GGTAAAAAAA CTATCTGAGT TGAAACTTCC AAAGAATCCT  1643
Gly Asp Phe Ser Thr Trp
                525

GAAGACAAAA AAAACTTCAT ATCCCATTAA AAAAAAAAAA AAAAAAAAAA AAG         1696

(2) INFORMATION FOR SEQ ID NO:2:

(i) SEQUENCE CHARACTERISTICS:
        (A) LENGTH: 527 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Gly Lys Lys Gln His Gln Lys Asp Lys Leu Tyr Leu Thr Thr Thr
1               5                   10                  15

Glu Trp Lys Glu Thr Tyr Gly Gly His Lys Asp Ser Thr Gly Arg Arg
                20                  25                  30

Ile Gln Arg Ala Leu Phe Lys Arg Leu Pro Ile Thr His Cys Ser Leu
            35                  40                  45

Ser Leu Leu Pro Phe Glu Asp Pro Val Cys Ser Arg Asp Gly Ile Ile
50                  55                  60

Phe Asp Leu Thr Gln Ile Ile Pro Tyr Leu Lys His Gly Val Asn
65                  70                  75                  80

Pro Val Thr Gly Lys Lys Met Thr Ala Lys Glu Leu Ile His Leu Lys
                85                  90                  95

Phe Asp Lys Asp Ala Asp Gly Asn Phe Arg Cys Pro Val Thr Phe Arg
            100                 105                 110

Thr Phe Thr Ala Thr Ser His Ile Val Ala Ile Cys Gln Thr Gly Asn
            115                 120                 125

Val Tyr Ser Leu Glu Ala Ile Glu Glu Leu Asn Leu Lys Pro Gly His
130                 135                 140

Leu Arg Asp Leu Leu Thr Asp Glu Pro Phe Gln Arg Lys Asp Ile Ile
145                 150                 155                 160

Thr Leu Gln Asp Pro Asn His Leu Glu Lys Phe Asn Ile Glu Gln Phe
                165                 170                 175

His His Val Lys Leu Asp Leu Lys Thr Lys Ala Glu Ile Glu Ala Glu
            180                 185                 190

Lys Lys Ala Met Glu Asp Pro Lys Phe His Ile Arg Trp Met Asn Asn
            195                 200                 205

Glu Thr Lys Glu Ile Leu Glu Lys Leu Ala Lys Glu Tyr Val Pro Thr
            210                 215                 220

Lys Ile Glu Glu Ile Glu Glu Ile Thr Asp Glu Leu Asn Ala Ala
225                 230                 235                 240

His Tyr Ser Gln Gly Arg Val Ala Ala Gly Leu Thr Ser Thr Thr Met
                245                 250                 255
```

-continued

```
Asp Pro Val Thr His Gln Lys Ala Ala Leu Asp Ala Asp Thr Val
            260                 265                 270

Lys Tyr Ala Arg Val Asn Lys Asn Gly Tyr Val Arg Ile Leu Thr Asn
        275                 280                 285

Tyr Gly Val Ile Asn Leu Glu Leu Phe Cys Lys Asp Ala Pro Arg Ala
        290                 295                 300

Cys Gly Asn Phe Ile Lys His Cys Lys Asn Gly Tyr Tyr Asn Asn Thr
305                 310                 315                 320

Lys Phe His Arg Ile Ile Arg Asn Phe Met Met Gln Gly Gly Asp Pro
                325                 330                 335

Thr Gly Thr Gly Lys Gly Gly Asp Ser Ile Trp Gly Lys Pro Phe Lys
            340                 345                 350

Asp Glu Phe Lys Ser Thr Phe Ser His Asp Arg Arg Gly Val Leu Ser
        355                 360                 365

Met Ala Asn Gln Gly Thr Asp Thr Asn Lys Ser Gln Phe Phe Ile Thr
    370                 375                 380

Phe Arg Ser Cys Ser Tyr Leu Asp Gly Lys His Thr Ile Phe Gly His
385                 390                 395                 400

Val Val Gly Gly Thr Gly Thr Leu Asn Thr Ile Glu Lys Ile Glu Thr
                405                 410                 415

Asp Glu Ser Gly Arg Pro Ile Val Asp Val Ile Phe Leu Asn Ala Glu
            420                 425                 430

Ile Phe Val Asp Pro Phe Glu Glu Ala Glu Lys Ala Val Glu Lys Glu
        435                 440                 445

Arg Glu Asn Ile Arg Leu Ala Lys Thr Asn Gln Glu Ser Glu Thr Ile
    450                 455                 460

Ala Asn Thr Pro Ala Thr Ala Val Gln Val Pro Lys Pro Lys Lys Tyr
465                 470                 475                 480

Gly Leu Gly Val Gly Lys Tyr Ile Asn Leu Pro Glu Val Val Ala Ala
                485                 490                 495

Thr Lys Arg Thr Ala Asn Asp Ile Ala Glu Phe Gly Val Pro Lys Lys
            500                 505                 510

Thr Ala His Cys Ala Asn Gln Ile Phe Gly Asp Phe Ser Thr Trp
        515                 520                 525

(2) INFORMATION FOR SEQ ID NO:3:

(i) SEQUENCE CHARACTERISTICS:
        (A) LENGTH: 527 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Gly Lys Lys Gln His Gln Lys Asp Lys Leu Tyr Leu Thr Thr Thr
1               5                   10                  15

Glu Trp Lys Glu Thr Tyr Gly Gly His Lys Asp Ser Thr Gly Arg Arg
            20                  25                  30

Ile Gln Arg Ala Leu Phe Lys Arg Leu Pro Ile Thr His Cys Ser Leu
        35                  40                  45

Ser Leu Leu Pro Phe Glu Asp Pro Val Cys Ser Arg Asp Gly Ile Ile
    50                  55                  60

Phe Asp Leu Thr Gln Ile Ile Pro Tyr Leu Lys Lys His Gly Val Asn
65                  70                  75                  80
```

-continued

Pro Val Thr Gly Lys Lys Met Thr Ala Lys Glu Leu Ile His Leu Lys
                85                  90                  95

Phe Asp Lys Asp Ala Asp Gly Asn Phe Arg Cys Pro Val Thr Phe Arg
            100                 105                 110

Thr Phe Thr Ala Thr Ser His Ile Val Ala Ile Cys Gln Thr Gly Asn
        115                 120                 125

Val Tyr Ser Leu Glu Ala Ile Glu Glu Leu Asn Leu Lys Pro Gly His
    130                 135                 140

Leu Arg Asp Leu Leu Thr Asp Glu Pro Phe Gln Arg Lys Asp Ile Ile
145                 150                 155                 160

Thr Leu Gln Asp Pro Asn His Leu Glu Lys Phe Asn Ile Glu Gln Phe
                165                 170                 175

His His Val Lys Leu Asp Leu Lys Thr Lys Ala Glu Ile Glu Ala Glu
            180                 185                 190

Lys Lys Ala Met Glu Asp Pro Lys Phe His Ile Arg Trp Met Asn Asn
        195                 200                 205

Glu Thr Lys Glu Ile Leu Glu Lys Leu Ala Lys Glu Tyr Val Pro Thr
    210                 215                 220

Lys Ile Glu Glu Ile Glu Glu Ile Thr Asp Glu Leu Asn Ala Ala
225                 230                 235                 240

His Tyr Ser Gln Gly Arg Val Ala Ala Gly Leu Thr Ser Thr Thr Met
                245                 250                 255

Asp Pro Val Thr His Gln Lys Ala Ala Ala Leu Asp Ala Asp Thr Val
            260                 265                 270

Lys Tyr Ala Arg Val Asn Lys Asn Gly Tyr Val Arg Ile Leu Thr Asn
        275                 280                 285

Tyr Gly Val Ile Asn Leu Glu Leu Phe Cys Lys Asp Ala Pro Arg Ala
    290                 295                 300

Cys Gly Asn Phe Ile Lys His Cys Lys Asn Gly Tyr Tyr Asn Asn Thr
305                 310                 315                 320

Lys Phe His Arg Ile Ile Arg Asn Phe Met Met Gln Gly Gly Asp Pro
                325                 330                 335

Thr Gly Thr Gly Lys Gly Gly Asp Ser Ile Trp Gly Lys Pro Phe Lys
            340                 345                 350

Asp Glu Phe Lys Ser Thr Phe Ser His Asp Arg Arg Gly Val Leu Ser
        355                 360                 365

Met Ala Asn Gln Gly Thr Asp Thr Asn Lys Ser Gln Phe Phe Ile Thr
    370                 375                 380

Phe Arg Ser Cys Ser Tyr Leu Asp Gly Lys His Thr Ile Phe Gly His
385                 390                 395                 400

Val Val Gly Gly Thr Gly Thr Leu Asn Thr Ile Glu Lys Ile Glu Thr
                405                 410                 415

Asp Glu Ser Gly Arg Pro Ile Val Asp Val Ile Phe Leu Asn Ala Glu
            420                 425                 430

Ile Phe Val Asp Pro Phe Glu Glu Ala Glu Lys Ala Val Glu Lys Glu
        435                 440                 445

Arg Glu Asn Ile Arg Leu Ala Lys Thr Asn Gln Glu Ser Glu Thr Ile
    450                 455                 460

Ala Asn Thr Pro Ala Thr Ala Val Gln Val Pro Lys Pro Lys Lys Tyr
465                 470                 475                 480

Gly Leu Gly Val Gly Lys Tyr Ile Asn Leu Pro Glu Val Val Ala Ala
                485                 490                 495

Thr Lys Arg Thr Ala Asn Asp Ile Ala Glu Phe Gly Val Pro Lys Lys

```
                   500             505             510
Thr Ala His Cys Ala Asn Gln Ile Phe Gly Asp Phe Ser Thr Trp
        515             520             525

(2) INFORMATION FOR SEQ ID NO:4:

(i) SEQUENCE CHARACTERISTICS:
         (A) LENGTH: 523 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:4:

Met Gly Lys Lys Gln His Gln Lys Asp Lys Leu Tyr Leu Thr Thr Ser
1               5                  10                  15

Glu Trp Lys Ser Ile Gly Gly His Lys Asp Asp Thr Gly Thr Arg Leu
            20                  25                  30

Gln Arg Ala Gln Phe Lys Arg Leu Pro Ile Asn His Cys Ser Leu Ser
        35                  40                  45

Leu Leu Pro Phe Glu Asp Pro Val Cys Ala Arg Ser Gly Glu Ile Phe
    50                  55                  60

Asp Leu Thr Ala Ile Val Pro Tyr Leu Lys Lys His Gly Lys Asn Pro
65                  70                  75                  80

Cys Thr Gly Lys Pro Leu Val Ala Lys Asp Leu Ile His Leu Lys Phe
                85                  90                  95

Asp Lys Gly Glu Asp Gly Lys Phe Arg Cys Pro Val Thr Phe Arg Thr
            100                 105                 110

Phe Thr Asp His Ser His Ile Leu Ala Ile Ala Thr Ser Gly Asn Val
        115                 120                 125

Tyr Ser His Glu Ala Val Gln Glu Leu Asn Leu Lys Arg Asn His Leu
    130                 135                 140

Lys Asp Leu Leu Thr Asp Val Pro Phe Thr Arg Ala Asp Ile Ile Asp
145                 150                 155                 160

Leu Gln Asp Pro Asn His Leu Glu Lys Phe Asn Met Glu Gln Phe Leu
                165                 170                 175

His Val Lys Leu Asp Leu Lys Thr Ser Glu Ile Lys Lys Glu Lys
            180                 185                 190

Asp Ala Met Lys Asp Pro Lys Phe Tyr Ile Arg Arg Met Asn Asn Ala
        195                 200                 205

Cys Lys Ser Val Leu Asp Gln Leu Asp Lys Glu Tyr Val Pro Lys Lys
    210                 215                 220

Ser Ser Thr Glu Thr Asp Glu Thr Ala Asp Glu Ile Asn Ala Ala His
225                 230                 235                 240

Tyr Ser Gln Gly Lys Val Ala Ala Gly Phe Thr Ser Thr Val Met Ala
                245                 250                 255

Pro Val Thr Ser Asn Lys Ala Ala Val Leu Asp Asn Asp Thr Val Arg
            260                 265                 270

Tyr Ser Arg Val Lys Lys Asn Ala Phe Val Arg Leu Val Thr Asn Phe
        275                 280                 285

Gly Pro Leu Asn Leu Glu Leu Phe Ala Pro Lys Val Pro Lys Ala Cys
    290                 295                 300

Glu Asn Phe Ile Thr His Cys Ser Asn Gly Tyr Tyr Asn Asn Thr Lys
305                 310                 315                 320

Phe His Arg Leu Ile Lys Asn Phe Met Leu Gln Gly Gly Asp Pro Thr
```

```
                    325                 330                 335
Gly Thr Gly His Gly Gly Glu Ser Ile Trp Asp Lys Pro Phe Ser Asp
                340                 345                 350
Glu Phe Ile Ser Gly Phe Ser His Asp Ala Arg Gly Val Leu Ser Met
                355                 360                 365
Ala Asn Lys Gly Ser Asn Thr Asn Gly Ser Gln Phe Phe Ile Thr Phe
                370                 375                 380
Arg Pro Cys Lys Tyr Leu Asp Arg Lys His Thr Ile Phe Gly Arg Leu
385                 390                 395                 400
Val Gly Gly Gln Asp Thr Leu Thr Thr Ile Glu Lys Leu Glu Thr Glu
                405                 410                 415
Glu Gly Thr Asp Val Pro Met Val Ser Val Val Ile Met Arg Ala Glu
                420                 425                 430
Val Phe Val Asp Pro Phe Glu Glu Ala Glu Lys Glu Val Gln Ala Glu
                435                 440                 445
Arg Ala Glu Ile Leu Lys Lys Thr Ser Lys Asp Ala Ala Ser Leu Ala
450                 455                 460
Asn Lys Lys Ala Lys Glu Thr Ala Thr Lys Pro Glu Ala Val Gly Thr
465                 470                 475                 480
Gly Val Gly Lys Tyr Met Lys Ser Ala Ala Val Asn Lys Arg Gln
                485                 490                 495
Gly Lys Met Glu Asp Val Pro Leu Glu Ala Ala Lys Lys Thr Lys Phe
                500                 505                 510
Ala Arg Ala Gly Leu Gly Asp Phe Ser Lys Trp
                515                 520

(2) INFORMATION FOR SEQ ID NO:5:

(i) SEQUENCE CHARACTERISTICS:
        (A) LENGTH: 520 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Gly Lys Arg Gln His Gln Lys Asp Lys Met Tyr Ile Thr Cys Ala
1                   5                  10                  15
Glu Tyr Thr His Phe Tyr Gly Gly Lys Lys Pro Asp Leu Pro Gln Thr
                20                  25                  30
Asn Phe Arg Arg Leu Pro Phe Asp His Cys Ser Leu Ser Leu Gln Pro
                35                  40                  45
Phe Val Tyr Pro Val Cys Thr Pro Asp Gly Ile Val Phe Asp Leu Leu
    50                  55                  60
Asn Ile Val Pro Trp Leu Lys Lys Tyr Gly Thr Asn Pro Ser Asn Gly
65                  70                  75                  80
Glu Lys Leu Asp Gly Arg Ser Leu Ile Lys Leu Asn Phe Ser Lys Asn
                85                  90                  95
Ser Glu Gly Lys Tyr His Cys Pro Val Leu Phe Thr Val Phe Thr Asn
                100                 105                 110
Asn Thr His Ile Val Ala Val Arg Thr Thr Gly Asn Val Tyr Ala Tyr
                115                 120                 125
Glu Ala Val Glu Gln Leu Asn Ile Lys Ala Lys Asn Phe Arg Asp Leu
                130                 135                 140
Leu Thr Asp Glu Pro Phe Ser Arg Gln Asp Ile Ile Thr Leu Gln Asp
```

```
145                 150                 155                 160
Pro Thr Asn Leu Asp Lys Phe Asn Val Ser Asn Phe Tyr His Val Lys
                165                 170                 175
Asn Asn Met Lys Ile Ile Asp Pro Asp Glu Glu Lys Ala Lys Gln Asp
            180                 185                 190
Pro Ser Tyr Tyr Leu Lys Asn Thr Asn Ala Glu Thr Arg Glu Thr Leu
        195                 200                 205
Gln Glu Leu Tyr Lys Glu Phe Lys Gly Asp Glu Ile Leu Ala Ala Thr
    210                 215                 220
Met Lys Ala Pro Glu Lys Lys Val Asp Lys Leu Asn Ala Ala His
225                 230                 235                 240
Tyr Ser Thr Gly Lys Val Ser Ala Ser Phe Thr Ser Thr Ala Met Val
                245                 250                 255
Pro Glu Thr Thr His Glu Ala Ala Ile Asp Glu Asp Val Leu Arg
            260                 265                 270
Tyr Gln Phe Val Lys Lys Gly Tyr Val Arg Leu His Thr Asn Lys
        275                 280                 285
Gly Asp Leu Asn Leu Glu Leu His Cys Asp Leu Thr Pro Lys Thr Cys
    290                 295                 300
Glu Asn Phe Ile Arg Leu Cys Lys Lys His Tyr Tyr Asp Gly Thr Ile
305                 310                 315                 320
Phe His Arg Ser Ile Arg Asn Phe Val Ile Gln Gly Gly Asp Pro Thr
                325                 330                 335
Gly Thr Gly Thr Gly Gly Glu Ser Tyr Trp Gly Lys Pro Phe Lys Asp
            340                 345                 350
Glu Phe Arg Pro Asn Leu Ser His Thr Gly Arg Gly Ile Leu Ser Met
        355                 360                 365
Ala Asn Ser Gly Pro Asn Ser Asn Arg Ser Gln Phe Phe Ile Thr Phe
    370                 375                 380
Arg Ser Cys Ala Tyr Leu Asp Lys Lys His Thr Ile Phe Gly Arg Val
385                 390                 395                 400
Val Gly Gly Phe Asp Val Leu Thr Ala Met Glu Asn Val Glu Ser Asp
                405                 410                 415
Pro Lys Thr Asp Arg Pro Lys Glu Glu Ile Arg Ile Asp Ala Thr Thr
            420                 425                 430
Val Phe Val Asp Pro Tyr Glu Glu Ala Asp Ala Gln Ile Ala Gln Glu
        435                 440                 445
Arg Lys Thr Gln Leu Lys Val Ala Pro Glu Thr Lys Val Lys Ser Ser
    450                 455                 460
Gln Pro Gln Ala Gly Ser Gln Gly Pro Gln Thr Phe Arg Gln Gly Val
465                 470                 475                 480
Gly Lys Tyr Ile Asn Pro Ala Ala Thr Lys Arg Ala Ala Glu Glu Glu
                485                 490                 495
Pro Ser Thr Ser Ala Thr Val Pro Met Ser Lys Lys Pro Ser Arg
            500                 505                 510
Gly Phe Gly Asp Phe Ser Ser Trp
        515                 520

(2) INFORMATION FOR SEQ ID NO:6:

(i) SEQUENCE CHARACTERISTICS:
        (A) LENGTH: 269 amino acids
        (B) TYPE: amino acid
        (C) STRANDEDNESS: single
        (D) TOPOLOGY: linear
```

(ii) MOLECULE TYPE: protein (xi) SEQUENCE DESCRIPTION: SEQ ID NO:6:

```
Met Ser Lys Lys Asp Arg Arg Val Phe Leu Asp Val Thr Ile Asp
 1               5                  10                  15

Gly Asn Leu Ala Gly Arg Ile Val Met Glu Leu Tyr Asn Asp Ile Ala
                20                  25                  30

Pro Arg Thr Cys Asn Asn Phe Leu Met Leu Cys Thr Gly Met Ala Gly
            35                  40                  45

Thr Gly Lys Ile Ser Gly Lys Pro Leu His Tyr Lys Gly Ser Thr Phe
50                  55                  60

His Arg Val Ile Lys Asn Phe Met Ile Gln Gly Gly Asp Phe Thr Lys
65                  70                  75                  80

Gly Asp Gly Thr Gly Gly Glu Ser Ile Tyr Gly Gly Met Phe Asp Asp
                85                  90                  95

Glu Glu Phe Val Met Lys His Asp Glu Pro Phe Val Val Ser Met Ala
            100                 105                 110

Asn Lys Gly Pro Asn Thr Asn Gly Ser Gln Phe Phe Ile Thr Thr Thr
        115                 120                 125

Pro Ala Pro His Leu Asn Asn Ile His Val Val Phe Gly Lys Val Val
130                 135                 140

Ser Gly Gln Glu Val Val Thr Lys Ile Glu Tyr Leu Lys Thr Asn Ser
145                 150                 155                 160

Lys Asn Arg Pro Leu Ala Asp Val Val Ile Leu Asn Cys Gly Glu Leu
                165                 170                 175

Val Arg Arg Lys Lys Arg Gln His Ser Ser Arg Ser Asn Glu Ser Val
            180                 185                 190

Ser Ser Ser Thr Ser Thr Glu Lys Ser His Lys Lys Thr Lys Lys Thr
        195                 200                 205

Lys Met Lys Glu Lys Lys Arg Lys Glu Ser Asp Glu Val Glu Gln Leu
    210                 215                 220

Glu Ile Gly Thr Val Val Pro Glu Ala Glu Leu Gln Leu Ser Ser Val
225                 230                 235                 240

Lys Ala Glu Asp Leu Pro Asp Glu Pro Asp His Gln Asn Lys Tyr Leu
                245                 250                 255

Met Arg Arg Ser Lys Thr Pro Glu Asn Ser Arg Lys Gly
            260                 265
```

(2) INFORMATION FOR SEQ ID NO:7:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Ser Arg Pro Lys Val Tyr Phe Asp Ile Thr Ile Asp Gly Ser Asn
 1               5                  10                  15

Ala Gly Arg Ile Val Met Glu Leu Phe Ala Asp Ile Val Pro Lys Thr
                20                  25                  30

Ala Glu Asn Phe Arg Cys Leu Cys Thr Gly Glu Arg Gly Val Gly Arg
            35                  40                  45

Ser Gly Lys Lys Leu His Tyr Lys Gly Ser Lys Phe His Arg Val Ile
```

```
                50                    55                    60
Pro Asn Phe Met Leu Gln Gly Gly Asp Phe Thr Arg Gly Asn Gly Thr
65                      70                      75                      80

Gly Gly Glu Ser Ile Tyr Gly Glu Lys Phe Pro Asp Glu Asn Phe Gln
                    85                      90                      95

Glu Lys His Thr Gly Pro Gly Val Leu Ser Met Ala Asn Ala Gly Pro
                100                     105                     110

Asn Thr Asn Gly Ser Gln Phe Phe Ile Cys Thr Ala Lys Thr Glu Trp
            115                     120                     125

Leu Asp Gly Lys His Val Val Phe Gly Arg Val Val Glu Gly Met Asn
            130                     135                     140

Val Val Lys Ala Ile Glu Ser Lys Gly Ser Gln Ser Gly Arg Thr Ser
145                     150                     155                     160

Ala Asp Val Val Ile Thr Asp Cys Gly Gln Leu
                165                     170
```

(2) INFORMATION FOR SEQ ID NO:8:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:8:

```
ATTTAACACA AATCATTCNN TATCTAAAAA AGNNTGGTTT NAATCCAGTA ACTGGCAAGA    60

AAATNACNGC AAAAGAATTG ATTCNTTTNA AATNCNNTAA AGATNCCGAT GGTAATTTNC   120

NNTNTCNTCT TACTTTCCAC TTTCACAGCN ACAGNCATAT GTGCA                  165
```

(2) INFORMATION FOR SEQ ID NO:9:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
ACGAGATGGA ATTATTTTTG ATTTAACACA AATCATTCCA TATCTAAAAA AGCATGGTGT    60

CAATCCAGTA ACTGGCAAGA AAATGACAGC AAAAGAATTG ATTCATTTGA AATTCGATAA   120

AGATGCCGAT GGTAATTTTC GATGTCCTGT TACTTTCCGT ACTTTCACAG CCACGAGTCA   180

TATTGTGGCC ATCTGTCAAA                                              200
```

(2) INFORMATION FOR SEQ ID NO:10:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CAGAATTCGG CGCGCCTGCA GGTTTAATTA CCCAAGTTTG AG                       42
```

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GGGATCCTCA AATGGCAGCA GTG       23

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CACTGCTGCC ATTTGAGGAT CCC       23

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TCCATAGCTT TTTTTTCAGC TTCAAT       26

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

ATGGACCCTG TAACACATCA GAAAGCAGCT       30

(2) INFORMATION FOR SEQ ID NO:15:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CGCAAGCTTA CCAAGTTGAG AAATCACCAA AAATCTG       37

(2) INFORMATION FOR SEQ ID NO:16:

(i) SEQUENCE CHARACTERISTICS:
        (A) LENGTH: 13 base pairs

```
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Arg Phe Met Gln Gly Ala Asp Gln Gln Phe Trp Leu His
 1               5                  10
```

TYROSINE-CONTAINING CYCLOPHILIN AND RELATED METHODS

BACKGROUND OF THE INVENTION

The present invention relates to a novel class of cyclophilins which contain a tyrosine residue as opposed to tryptophan or histidine in the drug binding site as well as to a method for identifying anti-parasitic compounds. More specifically, the present invention relates to a method for the identification of compounds capable of binding and/or inhibiting cyclophilins containing a tyrosine residue in lieu of tryptophan/histidine in the drug binding pocket, as well as to methods of treating parasitic infections which are not susceptible to cyclosporin A.

Cyclosporin A (CsA) is a lipophilic, 11 amino acid cyclic peptide originally isolated from the fungus *Tolypocladium inflatum*. Its immunosuppressive properties were first described in 1978 (Borel, *Pharmacol. Rev.* 41:259–371 (1990)) and it is currently the drug of choice in transplantation surgery and in the treatment of various autoimmune diseases (Kahan, "Cyclosporin: Biological activity and clinical applications," Grune and Stratton, Orlando, Fla. (1983)).

In 1984 the receptor for CsA was identified and purified from bovine spleen, and named cyclophilin A (CypA) (Handschumacher, et al., *Science*, 226:544–547 (1984)). CypA is an 18-kDa cytoplasmic protein (Haendler, et al., *EMBO. J*, 6:947–950 (1987)) that is abundantly expressed in all mammalian tissues (Koletsky, et al., *J. Immunol.* 137:1054–1059 (1986)). More recently, other cyclophilin isoforms have been described which share the highly conserved 18-kDa domain flanked by unique domains which are thought to function in organelle and membrane targeting of the protein (Gething, et al., *Nature* 355:33–45 (1992), Price, et al., *PNAS*, 88:1903–1907 (1991), Spik, et al., *J. Biol. Chem.* 266:10735–10738 (1991), Friedman, et al., *Cell* 66:23204–23214 (1991), and Bergsma, et al., *J. Biol. Chem.* 266:23204–231214 (1991)). These include from humans the larger Cyp-40 (40 kDa) (Kieffer, et al., *J. Biol. Chem.* 267:5503–5507 (1992)) and Cyp-60 (60 kDa) (Wang, et al., *Biochem. J.* 314:313–319 (1996)) proteins, and the surface-associated natural killer (NK) cell cyclophilin (150 kDa) (Anderson,.et al., *PNAS, USA* 90:542–546 (1993)).

Cyclophilins have also been found in several parasites including *Schistosoma mansoni* (Koletsky, et al., *J. Immunol,* supra, Klinkert, et al., *Mol. Biochem. Parasitol.,* 75:99–111 (1995), Kiang, et al., *Mol. Biochem. Parasitol.,* 76:73–82 (1995)), *Echinococcus granulosus* (Lightowlers, et al., *Mol. Biochem. Parasitol.,* 36:287–289 (1989), *Schistosoma japonicum* (Argaet, et al., *J. Parasitol.,* 78:660–664 (1992)), *Toxoplasma gondii* (High, et al., *J. Biol. Chem.,* 269:9105–9112 (1994)), *Plasmodium falciparum* (Bell, et al., *Biochem. Pharmacol.,* 48:495–503 (1994) and Reddy, et al., *Mol. Biochem. Parasitol.,* 73:111–121 (1995)), *Hymenolepis microstoma* (Roberts, et al., *Parasitology,* 111:591–597 (1995)), and the filarial worms *Brugia malayi* (Ma, et al., *Mol. Biochem. Parasitol.,* 79:235–241 (1996) and Page, et al., *Parasitol. Today,* 11:385–388 (1995)), *Onchocerca volvulus* and *Dirofilaria immitis* (Ma, et al., *Mol. Biochem., Parasitol.* supra and Hong, et al., *Exp. Parasitol.,*in press). Multiple isoforms can exist in parasites since 2 forms have been found in *T. gondii* (High, et al., *J. Biol. Chem.,* supra) and filarial parasites (Ma, et al., *Mol. Biochem. Parasitol,* supra, Hong, et al., *Exp. Parasitol,* in press, supra, and Page, et al., *Biochemistry,* 34:11545–11550 (1995)).

In addition to binding CsA, CypA was subsequently shown to possess an enzymatic activity (Fischer, et al., *Biomed. Biochim. Acta,* 43:1101–1111 (1984)). Fischer and coworkers characterized a new enzyme from pig kidney which was capable of catalyzing the cis to trans interconversion of proline containing peptides, and hence named it peptidyl-prolyl cis-trans isomerase (PPlase). Subsequent N-terminal peptide sequencing of this enzyme revealed that it was identical to cyclophilin (Lang, et al., *Nature,* 329:268–270 (1987)).

PPlases catalyse the cis-trans isomerisation of proline-imidic peptide bonds in oligopeptides and accelerate the refolding of several proteins in vitro (Gething, et al., *Nature,* supra, Lang, et al., *Nature,* 329:268–270 (1987) and Fransson, et al., *FEBS Lett.,* 296:90–94 (1992)) and in vivo (Lodish, et al., *J. Biol. Chem.,* 266:14835–14838 (1991) and Steinmann, et al., *J. Biol. Chem.,* 266:1299–1303 (1991)). PPlases also function as protein chaperones (Freskgard, et al., *Science,* 258:466–468 (1992) and Rinfret, et al., *Biochemistry,* 33:1668–1673 (1994)). These properties suggest that cyclophilins may also have a critical role in parasite development.

Every cyclophilin examined to date has PPlase activity, including the CypA homologs present in *S. mansoni* (Koletsky, et al, *J. Immunol.,* supra),T. gondii (High, et al., *J. Biol. Chem.,* supra) and *P. falciparum* (Bell, et al.,*Biochm. Pharmacol.,* supra). Recombinant *B. malayi* cyclophilins were also found to possess high levels of PPlase activity (Ma, et al., *Mol. Biochem., Parasitol,* supra and Page, et al., *Biochemistry,* supra).

In most cases, drug binding results in inhibition of PPlase activity (Takahashi et al., *Nature,* 337:473–475 (1989). X-ray crystallography (Pflugl, et al., *Nature,* 361:91–94 (1993) and site-directed mutagenesis studies (Liu, et al., *Biochemistry* 30:2305–2310 (1991)) have determined that 13 specific residues comprise the drug binding site of CypA, namely, Arg-Phe-Met-Gln-Gly-Ala-Asp-Gln-Gln-Phe-Trp-Leu-His (SEQ ID NO:16). These residues are highly conserved among most cyclophilin isoforms and homologs. Liu and coworkers demonstrated that the tryptophan residue at position 121 of CypA is particularly important for drug binding. The same 13 amino acids, notably including tryptophan, are found in the CsA-sensitive cyclophilins from *E. granulosus* (Lightowlers, et al., *Mol Biochem. Parasitol,* supra), *T. gondii* (Argaet, et al., *J. Parasitol.,* 78:660–664 (1992), *P falciparum* (Bell, et al., *Biochem., Pharmacol.,* surpa, Reddy, *Mol. Biochem. Parasitol.,* 73:111–121 (1995)), and the filarial Cyp-2 cyclophilins (Ma, et al., *Mol. Biochem., Parasitol.,* supra). Cyclophilins which have a residue other than tryptophan in the critical position have been reported. Human Cyp-40 (Kietten, et al., *J. Biol. Chem.,* supra) and NK cell cyclophilin (Anderson, et al., *PNAS,* supra) have histidine, and human Cyp-60 (Wang, et al.,*Biochem. J.,* supra) has a tyrosine residue in this position. The Cyp-1 proteins from filarial parasites (Page, et al., *Biochemistry,* supra, Hong, et al.,*Exp. Parasitol.,* supra) and certain cyclophilins from *C. elegans* (Page, et al., *Biochem. J.,* 317:179–185 (1996)) also have a histidine residue in the critical position. We have determined that this amino acid difference was shown to be responsible for the lack of sensitivity of the Cyp-1 PPlase activity to inhibition with CsA Various cDNA libraries of *B. malayi* and *O. volvulus* are currently being analyzed through tag sequencing (EST) analysis and sequences deposited in GenBank (Blaxter, et al., *Mol. Biochem. Parasitol.,* 77:77–93 (1996). Sequences related to both human Cyp-60 ('tyrosine-containing' cyclophilin) and a PPlase from *Schizosaccharomyces pombe* ('histidine-containing' cyclophilin) have been found in *B.* malayi (accession numbers W15136, AA111775) and *O. volvulus* (accession number AA294728). Based on these sequence deposits alone, there is insufficient information available to identify any of these sequences as belonging to 'tyrosine-containing' cyclophilins. In accordance with the present invention, it has been determined that these 3 partial sequences are related to DiCyp-3.

CsA has also been demonstrated to posses a broad spectrum anti-parasitic activity (Page, et al., *Parasitol. Today*, supra, and Chappell, et al., *Parasitology*, 105 Supplement, S25–S40 (1992)). The parasites *S. mansoni* (Bueding, et al., *Agents Actions* 11:380–383 (1981)), *T. gondii* (Mack, et al., *Antimicrob Agents Chemother*, 26:26–30 (1984) and McCabe, et al., *Transplantation*, 41:611–615 (1986)) and *P. falciparum* (Thommen-Scott, Agents Actions, 11:770–773 (1981)) are adversely affected by the drug and the PPlase activity of their cyclophilins is strongly inhibited by nanomolar concentrations of CsA (Koletsky, et al., *J. Immunol.*, supra, High, et al., *J. Biol. Chem.*, supra, Bell, et al., *Biochem. Pharmacology*, supra, Reddy, et al., *Mol. Biochem. Parasitol.*, supra). More recently, a non-immunosuppressive derivative of CsA was demonstrated to have potent activity against malaria parasites (Bell, et al., *Biochem. Pharmacol.*, supra). In contrast, *Brugia malayi* (Page, et al., *Parasitol. Today*, supra) is not susceptible to CsA, and previous studies have shown that this parasite possesses both a CsA-insensitive (Cyp-1) (Page, et al., *Biochemistry*, supra) and -sensitive (Cyp-2) cyclophilin (Ma, et al., *Mol. Biochem., Parasitol.*, supra). Cyp-1 was demonstrated to have a histidine residue in the critical tryptophan position (Page, et al., *Biochemistry*, supra, U.S. Pat. No. 5,482,850). We have determined using site-directed mutagenesis studies that the histidine residue is responsible for drug insensitivity. Cyp-1 and Cyp-2 homologs have also been identified in *O. volvulus* and *D. immitis* (Ma, et al., *Mol. Biochem., Parasitol*, supra and Hong, et al., *Exp. Parasitol.*, supra).

For tyrosine-containing cyclophilin (Cyp-3) described by the present inventors it would be desirable to have a compound that inhibits the PPlase activity of these proteins. Such a compound may be used to treat parasites which are not susceptible to the anti-parasitic effects of CsA.

It would also be desirable to have a method which can be used to readily screen and select compounds that are capable of binding tyrosines-containing cyclophilins from parasites which are not susceptible to the anti-parasitic effects of CsA and/or which inhibit the PPlase activity of such proteins. More specifically, it would be desirable to have a method which can be used to screen and select CsA derivatives that are capable of binding such cyclophilins and inhibiting PPlase activity while having reduced immunosuppressive activity on the host.

SUMMARY OF THE INVENTION

In accordance with the present invention, it has been discovered that parasites which are not susceptible to the anti-parasitic effects of CsA possess cyclophilins in which the conserved tryptophan at the CsA binding domain has been substituted with another amino acid, in particular substituted with tyrosine. The present invention relates to these novel cyclophilins as well as to the use of these 'tyrosine-containing' cyclophilins in a method for identifying compounds capable of binding to and/or inhibiting the enzymatic activity of these proteins. Such compounds may be further screened for their ability to adversely affect parasites which are not susceptible to the anti-parasitic effects of CsA.

Generally, this method comprises contacting a 'tyrosine-containing' cyclophilin with a compound to be tested (test compound) and measuring, binding and/or the change in enzymatic activity. Such methods may include the following general methods for drug discovery, familiar to the skilled artisan, but not limited to, using the tyrosine-containing cyclophilin to screen natural products (Hazuda, et al., *Drug Des. Discov.*, 15:17–24 (1997)), any type of combinatorial library of synthetic molecules (Hazuda, et al., *Drug Des. Discov.*, supra, Lam, *Anticancer Drug Des.*, 12:145–167 (1997)), phage display libraries (Fang, et al., *Biochem. Biophys. Res. Commun.*, 220:53–56 (1996)). Because of the high degree of homology between cyclophilins, preferably, the test compound is a CsA derivative. Most preferably, the CsA derivative is a binding site derivative. In particular, this method can be used (i) to screen for CsA derivatives capable of binding to filarial 'tyrosine-containing' cyclophilins that inhibit PPlase activity and (ii) to select those which are less or non-immunosuppressive to the host.

In a preferred embodiment, a fusion protein comprising the 'tyrosine-containing' cyclophilin and protein having binding affinity for a substrate, e.g., malE, is used in an affinity chromatography system to screen and select binding compounds. In this method, the fusion protein is contacted with a substrate to which the binding protein has specific affinity such that the fusion protein is reversibly affixed to the column. A test compound is then added to the column. The compound may be labeled. The column is then washed and analyzed to determine the presence of the compounds. Compounds found to have binding affinity for the fusion protein can then be tested for the ability to inhibit PPlase activity.

One 'tyrosine-containing' cyclophilin useful in the method of the present invention is from a parasitic nematode, *Dirofilaria immitis*, the causative agent of heartworm disease in dogs and cats. Others include the 'tyrosine-containing' cyclophilin from the human parasites *Onchocerca volvulus* and *Brugia malayi*.

The present invention further relates to the use the DNA encoding the *D.immitis* 'tyrosine-containing' cyclophilin, or a fragment thereof, in the identification and isolation of related genes from other organisms, including other species of parasitic nematodes. The present inventors have determined the presence of related genes by PCR in *B.malayi* and *O.volvulus*. These genes will hybridize to the *D. immitis* 'tyrosine-containing' cyclophilin under suitable conditions described in the Examples below.

BRIEF DESCRIPTION OF THE DRAWINGS

FIG. 1 is the nucleotide (SEQ ID NO:1) and deduced amino acid sequence (SEQ ID NO:2) of *D.immitis* 'tyrosine-containing' cyclophilin.

FIG. 2 is alignment of the deduced amino acid sequences (SEQ ID NO:3; SEQ ID NO:4; SEQ ID NO:5; SEQ ID NO:6; and SEQ ID NO:7) of various cyclophilins. The amino acid sequence of the *Dirofilaria immitis* cyclophilins are denoted DiCyp-3 (AF000668), DiCyp-2 (U47813); *Brugia malayi*, BmCyp-1 (L37292); Human nuclear-specific cyclophilin, HCyp-60 (U37219); *Caenorhabditis elegans*, CeCyp-4 (Z46935, Z36949, U36187). C-terminal asterisks indicate translational terminations. In the Cyp-1 sequences the additional C-terminal residues are not shown. Dashes indicate residues identical to the corresponding residue in DiCyp-3. Dots denote gaps. The residues important in cyclosporin A binding are indicated with a "#".

FIG. 4 shows a comparison of the nucleotide sequence of the *O. volvulus* PCR Fragment (SEQ ID NO:8) and DiCyp-3 (SEQ ID NO:9).

Figure 5:
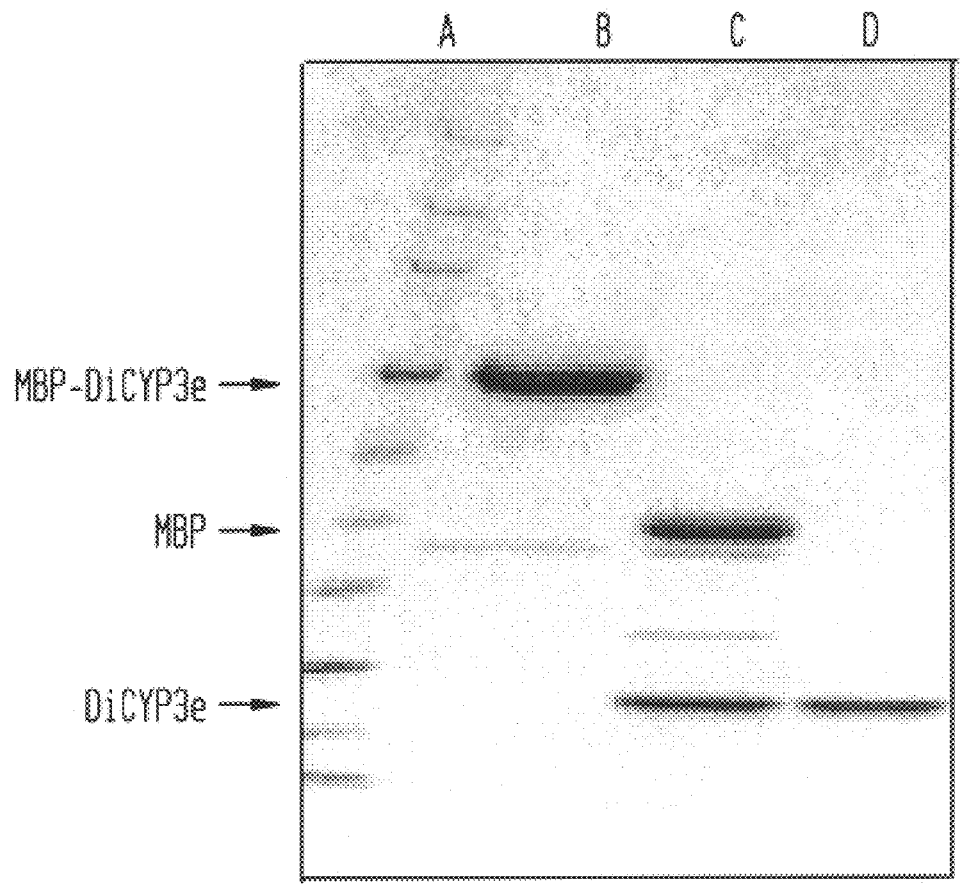

FIG. 5 shows the expression of DiCyp-3 in the maltose binding fusion protein system. Molecular weight markers (lane A), fusion protein (lane B), fusion protein cut with Factor Xa (lane C) and purified Cyp-3 (lane D) are shown.

Figure 6:
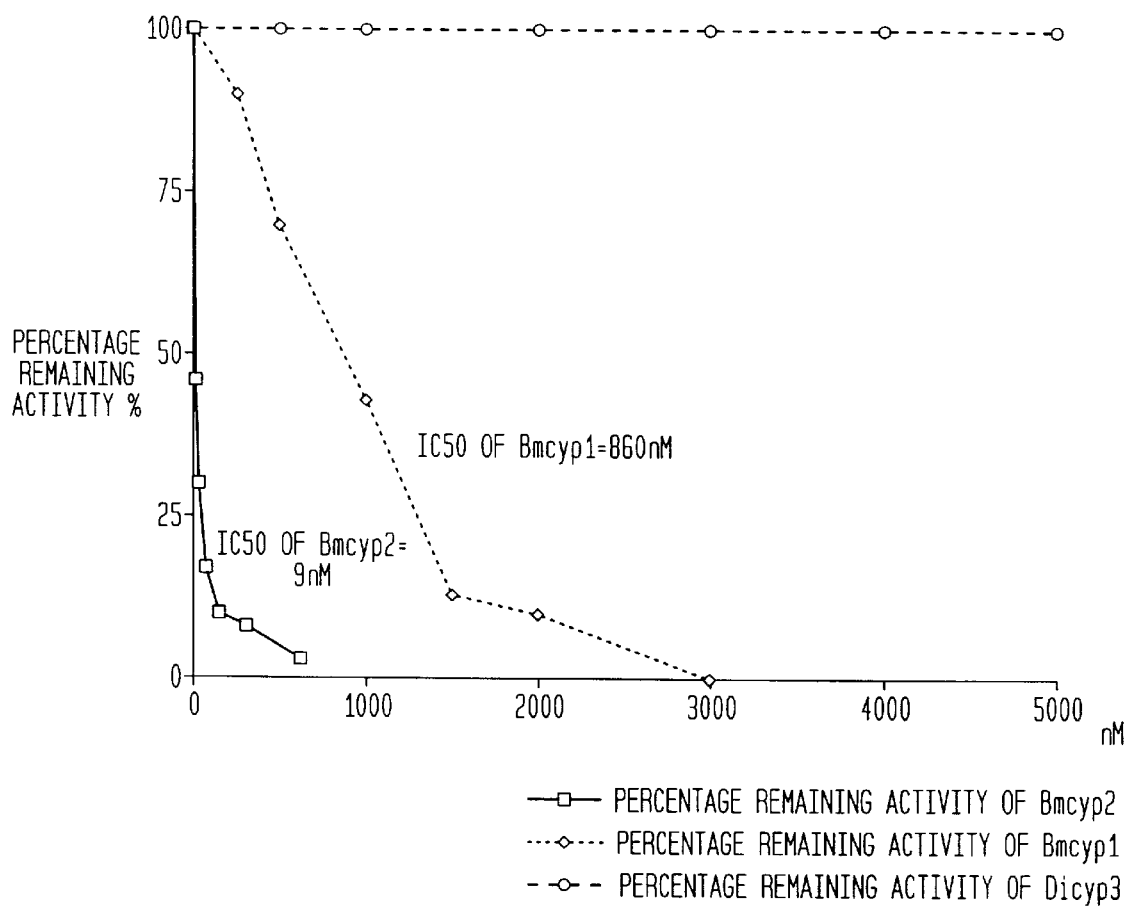

FIG. 6 shows inhibition of the PPlase activity of filarial cyclophilins using CsA. The $IC_{50}$ of BmCyp-1 and BmCyp-2 are shown.

FIG. 7 shows substrate specificity of filarial cyclophilins toward various peptide substrates. BmCyp-1, BmCyp-2 and DiCyp-3 were analyzed.

DETAILED DESCRIPTION OF THE INVENTION

The present invention relates to 'tyrosine-containing' cyclophilins and their use in a method for identifying compounds capable of binding to and/or inhibiting the enzymatic activity of these proteins. As noted above, a 'tyrosine-containing' cyclophilin is a cyclophilin wherein the conserved tryptophan at the CsA drug binding domain has been substituted by tyrosine. Compounds which bind 'tyrosine-containing' cyclophilins may be further screened for their ability to adversely affect parasites which are not susceptible to the anti-parasitic effects of CsA as discussed in more detail below.

Generally, the method for identifying compounds capable of binding to and/or inhibiting the enzymatic activity of these proteins comprises contacting a 'tyrosine-containing' cyclophilin, e.g., the *D.immitis* 'tyrosine-containing' cyclophilin, with a compound to be tested (test compound) and measuring the binding and/or inhibiting the enzymatic activity. The 'tyrosine-containing' cyclophilin may be affixed to a solid phase using, for example, an affinity chromatography system.

Using the method of the present invention, any test compound may be tested. The test compound may be a natural product (Hazuda, et al., *Drug Des. Discov.* supra), from any type of combinatorial library of synthetic molecules (Hazuda, et al., *Drug Des. Discov.,* supra, Lam, *Anticancer Drug Des.,* supra) or from phage display libraries (Fang, et al., *Biochem. Biophys. Res. Commun.,* 220:53–56 (1996)). Preferably, the test compound is an CsA derivative. See, for example, Borel, *Transplantation Proc.,* 21:810–815 (1989). By the term CsA derivative it is meant a compound having one or more amino acid substitutions, or amino deletions, from the structure of CsA, as well as modified amino acids. A number of CsA derivatives have been reported. See, e.g., Merck Index, pg. 431, 2759 (11th ed. 1989); Nelson, et al., *Journal of Immunology,* 150:2139–2147 (1993). Other CsA derivatives may be prepared using known synthetic methods. See, Nelson, et al, supra.

Most preferably, the CsA derivative is a binding site derivative. (Pfugl et al *Nature* (London) 361, 91–94 (1993)). Other potential target include cyclic undecapeptides.

Compounds may also be designed that inhibit the PPlase activity of 'tyrosine-containing' cyclophilins. The crystal structure of 'tryptophan-containing' cyclophilin has been resolved as both a free form (Pfugl et al *Nature* (London) 361, 91–94 (1993)) and as a complex with CsA (Kallen, et al., *Nature,* 353:276–279 (1991); Kallen & Walkinshaw, *FEBS Letters,* 300:286–290 (1992); Pflugl, et al., *Nature,* 361:91–94 (1993)). These studies were performed in order to design analogs of CsA with less toxic side effects in humans. Structure-based drug design can be employed in the same manner using three-dimensional structural information about 'tyrosine-containing' cyclophilins. Computer analysis of the 'tyrosine-containing' cyclophilin structure and use of computer programs, for example, DOCK3.5, may predict potential inhibitors that can then be tested using the method of the present invention. For example, the modeled active sites of cysteine proteases from *Leishmania major* were used to screen the Available Chemicals Directory (a database of approximately 150,000 commercially-available compounds). Several inhibitors were found (Seizer, et al., *Exp. Parasitol.,* 87:212–221 (1997)).

Compounds showing promising activity can be further screened for in vitro and in vivo inhibition of parasitic nematode growth using, for example, the methods of Riberu, et al., *Am. J. Trop. Med. Hyg.,* 43:3–5 (1990) and Denham *Animal Models in Parasitology,* ed. D. Owen, p. 93, MacMillan, London (1982).

In one embodiment, a fusion protein comprising the 'tyrosine-containing' cyclophilin and protein having binding affinity for a substrate, e.g., malE, is used in an affinity chromatography system to screen and select binding compounds. Techniques for forming fusion proteins are well known to the skilled artisan. See, U.S. Pat. No. 5,643,758 and J. Sambrook, et al., *Molecular Cloning: A Laboratory Manual,* Cold Spring Harbor Laboratory Press, Cold Spring Harbor, N.Y., p. 17.29–17.33 (1989). For convenience, commercially available systems may be used, including, for example, the Protein Fusion and Purification System from New England Biolabs (Beverly, Mass.; U.S. Pat. No. 5,643, 758).

The fusion protein is then contacted with a substrate to which the binding protein has specific affinity such that the fusion protein is reversibly affixed to the column. A test compound is then added to the column. The compound may be labeled. The column is then washed and analyzed to determine the location of the compounds. Compounds found to have binding affinity for the fusion protein can then be tested for the ability to inhibit PPlase activity. (Maina, et al., *Gene,* 74:365–373 (1988)). The skilled artisan would appreciate that other commercially-available systems may be employed as described above, for example, the Gene Fusion System (GST) (Pharmacia, (Piscataway, N.J.) and the Fusion Tag System (Novagen, Madison, Wis.). Non-fusion systems may also be used, for example, the IMPACT™ system (New England Biolabs, Inc., Beverly, Mass.).

Binding proteins which may be employed in the method of the present invention include, for example, sugar binding proteins, such as maltose or arabinose binding protein, receptor binding proteins, amino acid binding proteins and metal binding proteins. Other binding proteins are well known to the skilled artisan. See, U.S. Pat. No. 5,643,758 and N. M. Sassenfeld, *TIB TECH* 8:88–93 (1990).

In a preferred embodiment, a fusion protein comprising the 'tyrosine-containing' cyclophilin (also referred to as DiCyp-3 or Cyp-3) and maltose binding protein (MBP) is used in an affinity chromatography system to screen and select binding compounds. For example, using the *D. immitis* 'tyrosine-containing' cyclophilin/MBP fusion described in detail in the Example which follows, affinity columns can be prepared which will selectively bind to compounds, specific for the tyrosine-containing drug binding domain of *D.immitis.*

The fusion protein is preferably loaded onto a amylose column which has been previously equilibrated with buffer. The test compounds are preferably added in equimolar ratios to the fusion protein, and can be tagged with a radioactive marker, such as a tritium. The columns are then washed with buffer and assayed both by scintillation counting and Bradford assay (Bradford, *Analytical Biochem.*, 72:248 (1976)) to determine radioactivity and protein release, respectively in the flow-through fractions.

In another embodiment, Cyp-3 protein in a purified or fusion-protein form may be used to select peptides or substances which bind in, for example, natural products, combinatorial libraries of synthetic molecules or phage libraries. For convenience, commercially-available systems may be used, for example, the Ph.D7 and Ph.D12 systems (New England Biolabs, Inc., Beverly, Mass.). Protein may be bound to plastic or beads and incubated with phage particles. After 3–4 rounds of amplification, peptides binding to Cyp-3 may be identified.

These methods can be used to determine which compounds, including cyclosporin A derivatives have the ability to bind to the 'tyrosine-containing' cyclophilin of *D.immitis* and the other 'tyrosine-containing' cyclophilins from other sources, including parasitic nematodes. Compound selected by this method can then be further analyzed for PPlase inhibitory activity using, for example, the method set forth below.

The peptidyl-prolyl cis-trans isomerase assay (PPlase) is the standard assay described by Fischer, et al., *Nature*, 337:476–478 (1989); Takahashi, et al., *Nature*, 337:473–475 (1989) with the modifications listed by Kofron, et al., *Biochemistry*, 30:6127–6134 (1991). A direct comparison of the enzyme kinetics of the 'tyrosine-containing' PPlase in the presence and absence of the test compound will reveal which compounds have PPlase inhibitory effects.

In another embodiment, the present invention relates a method of inhibiting the growth and development of parasites which are not susceptible to CsA. Generally, this method comprises contacting a parasite with, or administering to a host infected with said parasite, an effective amount of a compound which binds to and inhibits 'tyrosine-containing' cyclophilin activity in accordance with the above-described methodology.

According to the present invention, an "effective amount" of a compound is an amount sufficient to achieve the desired inhibition of parasite growth or death. It will be appreciated that the actually preferred amounts of compounds used will vary according to the specific compound being utilized, the particular compositions formulated and the mode of administration.

The compounds can be contacted with a parasite or administered to a host by any known means. For example, the compound may be directly administered to a parasite in culture. When the compound is administered to a host, any of a variety of means may be used, for example, parenteral injection (intramuscular (I.M.), intraperitoneal (I.P.), intravenous (I.V.), intracranial (I.C.) or subcutaneous (S.C.)), oral, inhaling through airways, or other known routes of administration.

The compounds can be administered in any means convenient, for example, it can be mixed with an inert carrier such as sucrose, lactose or starch. It can be in the form of tablets, capsules and pills. For parenteral administration, it will typically be injected in a sterile aqueous or non-aqueous solution, suspension or emulsion in association with a pharmaceutically-acceptable parenteral carrier such as physiological saline. Suitable pharmaceutical compositions can be formulated in accordance with known techniques such as those used in the formulation of CsA.

One 'tyrosine-containing' cyclophilin useful in practicing the methods of the present invention is the 'tyrosine-containing' cyclophilin from a parasitic nematode, *D.immitis*, the heartworm. This protein comprises 527 amino acids and has a predicted molecular weight of about 60 kDa. The DNA encoding the 'tyrosine-containing' cyclophilin from *D.immitis* can be obtained from a 1584 bp cDNA inserted in pMal-c2 resulting in a plasmid designated DiCyp-3. A sample of an *E. coli* ER 2688 transformed with plasmid DiCyp-3 has been deposited with the American Type Culture Collection (ATCC) under the Budapest Treaty on Feb. 24, 1998 and received ATCC Accession No. 98674. The nucleotide sequence of the 1584 bp cDNA insert is set forth in the Sequence Listing as SEQ ID NO:1. The *D.immitis* 'tyrosine-containing' cyclophilin amino acid sequence is set forth in the Sequence Listing as SEQ ID NO:2. Sequence analysis demonstrates that the *D.immitis* 'tyrosine-containing' cyclophilin has a tyrosine residue (Tyr 390) in place of the conserved tryptophan, established as being essential for binding to the drug CsA in other cyclophilins. The residues involved in drug binding are indicated as "#" in FIG. 2.

The DNA encoding the *D.immitis* 'tyrosine-containing' cyclophilin was isolated from an adult *D.immitis* cDNA library using as a probe affinity purified dog antibody (Hong, et al., *Parasitology*, 112:3431–338 (1996)) (see, Example 1).

The DNA encoding the *D.immitis* 'tyrosine-containing' cyclophilin, or a fragment thereof, can be used in the identification and isolation of related genes from other organisms, including other parasitic nematodes. For example, gene-specific primers can be used in PCR reactions to determine the presence of related genes in other organisms. In addition, DNA can be used in a Southern blot to screen for related genes from other organisms.

A number of techniques familiar to the skilled artisan can be used to isolate DNA sequences corresponding to related 'tyrosine-containing' cyclophilin genes. For example, a cDNA or expression library may be produced in a conventional manner by reverse transcription from messenger RNA (mRNA) from an organism found to possess related sequences, for example, by PCR or Southern blot analysis.

To select clones containing DNA sequences encoding 'tyrosine-containing' cyclophilins, hybridization probes corresponding to portions of the Cyp-3 cDNA are produced and used to identify clones containing such sequences as described in the Example below. Preferable probes include, but not restricted to, a fragment from nucleotide 503 to nucleotide 875 of SEQ ID NO:1. Screening of the expression library with antibodies generated against the *D.immitis* 'tyrosine-containing' cyclophilin, or a fragment thereof, may also be used. Genomic libraries may also be used. Such techniques are taught, for example, in Sambrook, et al., *Molecular Cloning*, Second edition, CSH Laboratory Press (1989).

If desired, the DNA thus obtained can then be sub-cloned for further manipulation using techniques familiar to the skilled artisan. For example, the DNA can be subcloned into a vector such as pBR322, pUC19 or T vector.

Once identified, the DNA sequence coding for the 'tyrosine-containing' cyclophilin can be cloned into an appropriate expression vector such as a plasmid derived from *E. coli*, for example, pET3A, pBluescript or pUC19, the plasmids derived from the *Bacillus subtilis* such as pUB110, pTP5 and pC194, plasmids derived from yeast such as pSH19 and pSH15, bacteriophage such as lambda phage, bacteria such as *Agrobacterium tumefaciens,* animal viruses such as retroviruses and insect viruses such as Baculovirus.

Overexpression of the 'tyrosine-containing' cyclophilin can be achieved, for example, by separating the 'tyrosine-containing' cyclophilin from its endogenous control elements and then operably linking the Cyp-3 or 'tyrosine-containing' cyclophilin gene to a very tightly controlled promoter such as a T7 expression vector. See, Rosenberg, et al., *Gene,* 56:125–135 (1987). Insertion of the strong promoter may be accomplished by identifying convenient restriction targets near both ends of the 'tyrosine-containing' cyclophilin gene and compatible restriction targets on the vector near the promoter, and transferring the 'tyrosine-containing' cyclophilin gene into the vector in such an orientation as to be under transcriptional and translational control of the strong promoter.

The 'tyrosine-containing' cyclophilin may also be overexpressed by utilizing a strong ribosome binding site placed upstream of the 'tyrosine-containing' cyclophilin gene to increase expression of the gene. See, Shine and Dalgarno, *Proc. Natl. Acad. Sci. USA,* 71:1342–1346 (1974).

The recombinant vector is introduced into the appropriate host using standard techniques for transformation and phage infection. For example, the calcium chloride method, as described by S. N. Cohen, *Proc. Natl. Acad. Sci. USA* 69:2110 (1972) is used for *E. coli,* the disclosure of which is incorporated by reference. The transformation of Bacillus is carried out according to the methods of S. Chang, et al., *Molecular and General Genetics,* 168:111 (1979). Transformation of yeast is carried out according to the method of Parent, et al., *Yeast,* 1:83–138 (1985). Certain plant cells can be transformed with *Agrobacterium tumefaciens,* according to the method described by C. H. Shaw, et al., *Gene,* 23:315 (1983),. Transformation of animal cells is carried out according to, for example, the method described in *Virology,* 52:456 (1973). Transformation of insect cells with Baculovirus is carried out according to, for example, the method described in *Biotechnology,* 6:47 (1988).

The transformants are cultivated, depending on the host cell used, using standard techniques appropriate to such cells. For example, for cultivating *E. coli,* cells are grown in LB media at 30° C. to 42° C. to mid log or stationary phase.

The 'tyrosine-containing' cyclophilin can be isolated and purified from a culture of transformed host cells, for example, by either extraction from cultured cells or the culture solution.

When the 'tyrosine-containing' cyclophilin is to be extracted from a cultured cell, the cells are collected after cultivation by standard methods, for example, centrifugation. Then, the collected cells are suspended in an appropriate buffer solution and disrupted by ultrasonic treatment, lysozyme and/or freeze-thawing. A crude extract containing the 'tyrosine-containing' cyclophilin is obtained by centrifugation and/or filtration.

When the 'tyrosine-containing' cyclophilin is secreted into the culture solution, i.e., alone or as a fusion protein with a secreted protein such as maltose binding protein, the supernatant is separated from the cells by standard methods.

The separation and purification of 'tyrosine-containing' cyclophilin contained in the culture supernatant or the cell extract can be performed by the method described above, or by appropriate combinations of known separating and purifying methods. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electric charge such as ion-exchange column chromatography, methods utilizing specific affinity chromatography, methods utilizing difference in hydrophobicity such as reverse-phase high performance liquid chromatography and methods utilizing a difference in isoelectric point such as isoelectric focusing electrophoresis.

The purified 'tyrosine-containing' cyclophilin can be used to produce antibodies, either polyclonal or monoclonal, useful as probes to detect and/or purify related cyclophilins in other parasites.

The present invention also relates to methods for the identification of 'tyrosine-containing' cyclophilins from other disease causing parasites of veterinary and medical importance. This method comprises using primers from a gene-specific region of the 'tyrosine-containing' cyclophilin, the amino acid sequence of the drug-binding domain can be determined in a variety of parasites responsible for important diseases. Those diseases caused by organisms which possess a tyrosine residue in place of tryptophan in the drug binding domain could potentially be treated with the compounds and analogs identified using the methods discussed above.

The present invention is further illustrated by the following Examples. These Examples are provided to aid in the understanding of the invention and are not construed as a limitation thereof.

The references cited above and below are herein incorporated by reference.

EXAMPLE 1

Isolation and Characterization of a DNA Encoding the *Dirofilaria Immitis* 'Tyrosine-Containing' Cyclophilin Screening a *D.Immitis* cDNA Library All reagents, kits and bacterial strains used in cloning and expression (below) were obtained from New England Biolabs (Beverly, Mass.) and used as described by the manufacturer, unless otherwise specified. A *D. immitis* adult worm cDNA library in λgt11 (Grandea et al., *Mol. Biochem. Parasitol.* 35:31–41 (1989)) was kindly provided by Dr. L. McReynolds and approximately 100,000 phage were immunoscreened with affinity purified dog antibodies (Hong, et al., *Parasitology,* supra).

An expression library of *D. immitis* or other nematodes could also be screened by hybridization using a DNA probe with SEQ ID NO:1, or part thereof. The probe could be a PCR fragment amplified from *D. immitis* using two specific primers. The PCR product would be purified using the Gene Clean Kit (Bio 101, Inc., Vista, Calif.) and 100 ng labelled with 50 $\mu$Ci ($\alpha$-$^{32}$P)dATP (NEN DuPont, Boston, Mass.) using the NEBlot® Kit (New England Biolabs, Inc., Beverly, Mass.). The probe would be purified from free counts on a Sephadex G-50 column (Pharmacia, Piscataway, N.J.).

Nitrocellulose filters would be prepared by Benton-Davis Plaque Lift Method (Benton & Davis, *Science,* 196:180–182 (1977)). Duplicate filters containing a total of 400,000 plaques would be prehybridized for 4 hours at 37° C. in hybridization solution (50% formamide, 1% SDS, 10% Denhardt's 5× SSC and 0.05 mg/ml of non-specific calf thymus DNA denatured by boiling in $H_2O$ for 10 minutes) and then hybridized with the $10 \times 10^6$ cpm's of $^{32}P$ labelled probe overnight at 37° C. in hybridization solution (same as above). The filters would be subsequently washed extensively in 0.1× SSC, 0.1% SDS for 5 minutes at room temperature for four changes; then in the same solution at 55° C. for 15 minutes with four changes, finally in 1× SSC for 5 minutes at room temperature with two changes.

Sequencing

For sequence analysis positive clones were subcloned into either pUC19 or the T vector using the protocol provided by the manufacturer (Promega, Madison, Wis.). The complete sequence of the cDNA encoding DiCyp3 was sequenced in both directions using the CircumVent™ Thermal Cycle Dideoxy DNA Sequencing Kit, or using an ABI 373A automated sequencer (PE Applied Biosystems; Foster City, Calif.) and Taq DyeDeoxy Terminator Cycle Sequencing Kit (PE Applied Biosystems; Foster City, Calif.).

DNA sequences were analyzed using the Genetics Computer Group (GCG) Software. Pairwise identity comparisons of DiCyp-3 to other cyclophilins were performed using the program GAP. Multiple alignment of the derived amino acid sequences of DiCyp-3 and other cyclophilins was made using the program PILEUP (gap weight=3.0, gap length weight=0.1).

Nucleotide and Deduced Amino Acid Sequence of DiCyp-3

A partial cDNA clone (636 bp) encoding a putative cyclophilin was isolated from a *D. immitis* adult worm cDNA library. To obtain a larger cDNA, the insert was used as a probe to rescreen 480,000 plaques from the same library under high stringency conditions. A total of 20 positive clones was obtained on duplicate filters. The clone with the largest insert (1619 bp) was selected but was found not to have a codon for an initiating methionine. The remaining clones also lacked the 5' end of the gene. Therefore, thermal cycling experiments were performed on the same cDNA library using a sense primer containing the nematode specific 22-nucleotide splice leader sequence [25] (underlined) (5'-CAGAATTCGGCGCGCCTGCAGGTTTAATT ACCCAAGTTTGAG-3' (SEQ ID NO:10)), and an antisense primer (5'-GGGATCCTCAAATGGCAGCAGTG-3' (SEQ ID NO:11)) with sequence derived from the partial cDNA. Products were subcloned into the T vector using the protocol provided by the manufacturer (Promega; Madison, Wis.) and sequenced. 77 additional nucleotides including the above splice leader sequence at the 5' end of the cDNA were obtained.

The nucleotide sequence of the complete DiCyp-3 cDNA clone has an ORF from bp 25 to 1605 (FIG. 1 (SEQ ID NO:1)). The resulting protein of 527 amino acids has a predicted molecular weight of 60 kDa. Pairwise identity comparisons of DiCyp-3 to other cyclophilins and multiple alignment of the derived amino acid sequences of DiCyp-3 and other cyclophilins revealed that DiCyp-3 represents a new class of parasite cyclophilin. The protein is 527 aa in size and has both N- and C-terminal (approximately 260 and 90 aa respectively) extensions. The previously described BmCyp-1 filarial cyclophilin possesses a large C-terminal extension of 666 aa whereas the Cyp-2 homologs exist as a PPlase domain alone. Most cyclophilins do not possess additional domains and the significance of their presence remains unclear.

DiCyp-3 shares only 46% and 51% similarity to DiCyp-1 (Hong, et al., *Exp. Parasitol.* in press) and DiCyp-2 (Ma, et al., *Mol. Biochem. Parasitol.,* supra), respectively. Likewise, a low level of similarity (66–69%) is found between the Cyp-1 and Cyp-2 homologs from *B. malayi, O. volvulus* or *D. immitis.* In contrast, the corresponding homologs of Cyp-1 (97–99%) (Hong, *Exp. Parasitol,* supra) or Cyp-2 (80–95%) (Ma, et al., *Mol. Biochem. Parasitol.,* supra) present in these 3 filarial species are highly similar to each other. In addition to its unique N- and C-terminal domains, the most important distinguishing feature of the new Cyp-3 cyclophilin lies in the composition of the drug-binding site. There are 13 residues that constitute the CsA-binding site of human cyclophilin A (Arg-Phe-Met-Gln-Gly-Ala-Asp-Gln-Gln-Phe-Trp-Leu-His (SEQ ID NO:16) and one of these residues (tryptophan$_{121}$), is essential for drug binding (Pflugl, et al., *Nature,* supra and Liu, et al., *Biochemistry,* supra). The same residues are found in Cyp-2 homologs of filarial parasites (FIG. 2 indicated #) and the majority of other parasite cyclophilins (Ma, et al., *Mol. Biochem. Parasitol.* supra). In the Cyp-3 cyclophilin, 11 of the 13 residues (arginine, phenylalanine, methionine, glutamine, glycine, alanine, asparagine, glutamine, phenylalanine, leucine, histidine) are conserved and, unlike any other parasite cyclophilin described to date, a tyrosine residue (Tyr$_{390}$) instead of tryptophan is present at the critical position in the drug binding site. Recently, two other cyclophilins have been described in *Caenorhabditis elegans* (CeCyp-4) (Page, et al., *Biochem. J.,* 317:179–185 (1996)) and humans (Cyp-60) (Wang, et al., *Biochem. J.* supra) which possess a tyrosine residue in this position. These proteins are similar in size to Cyp-3, also possess N- and C-terminal extensions, and are 66% and 52% identical to Cyp-3 at the amino acid level, respectively. No drug binding studies have been reported on either CeCyp-4 or human Cyp-60.

The absence of this CsA binding dependent residue led to the hypothesis that the *D.immitis* protein would have a reduced or absent affinity for this drug.

EXAMPLE 2

Presence of Cyp-3 Related Genes in Other Parasites

Polymerase Chain Reaction

Specific primers corresponding to a region of the N-terminal extension of DiCyp-3, were used to determine the presence of related genes in *B. malayi* and *O. volvulus.* The sequences of the sense primer (5'-CACTGCT GCCATTTGAGGATCCC-3' (SEQ ID NO:12)) and antisense primer (5'-TCCATAGCTTTTTTTTCAGCTTCAAT-3' (SEQ ID NO:13)) corresponded to bp 170–192 and 589–614 of DiCyp-3 (FIG. 1), respectively. PCR was performed using Deep Vent™ DNA polymerase on 1.5 µl of cDNA library stock (*B. malayi* L3 cDNA library or *O. volvulus* L3 cDNA library) at 95° C./1 min., 37° C. or 45° C./1 min., 72° C./2 min. for 30 cycles followed by 72° C. for 5 min.

Figure 3:
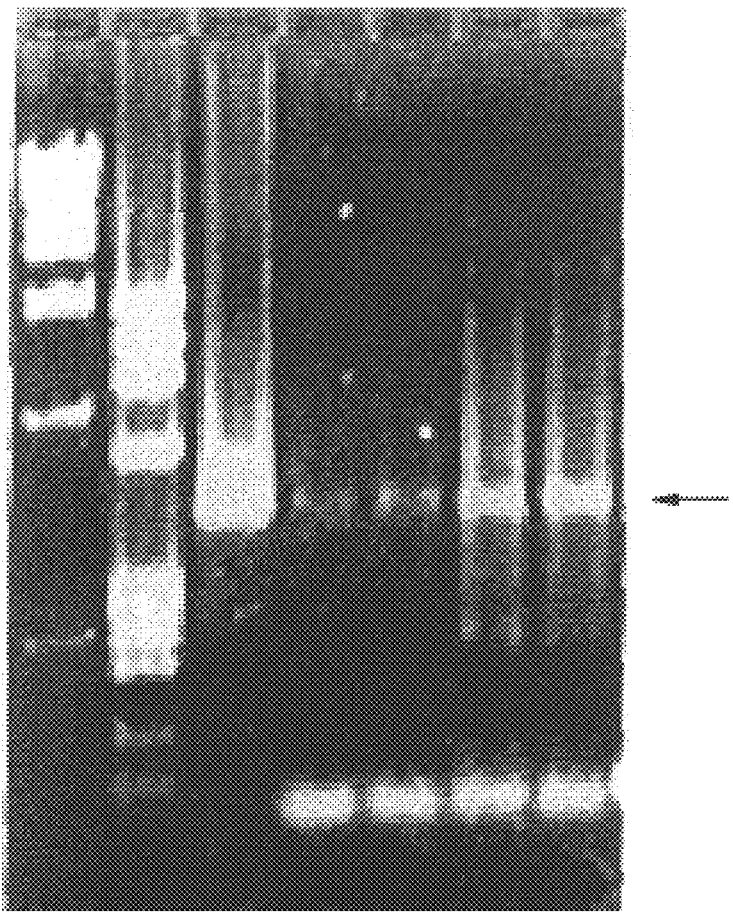
FIG. 3 shows a 1.5% agarose gel containing PCR products from *B. malayi* and *O. volvulus*. A single band of 438 bp is prsent in *D. immitis* (lane C), *O. volvulus* (lane D and lane E) and *B. malayi* (lane F and lane G).

The PCR products were then analyzed on a 1.5% agarose gel and a single band of an appropriate size was observed in *B. malayi* and *O.volvulus* (FIG. 3).

The *O. volvulus* PCR product was then run on a 1% low melt-point agarose gel, excised and digested for 30 min with 2U of β-agarase (New England Biolabs, Inc.; Beverly, Mass.). The supernatant was phenol extracted and ethanol precipitated, and then resuspended in distilled water. The PCR fragment was subcloned into pUC 19 for sequence analysis.

The DNA sequence obtained (FIG. 4) was 93% similar to the DiCyp-3 sequence in FIG. 1 demonstrating that *O. volvulus* possesses a 'tyrosine-containing' cyclophilin.

EXAMPLE 3

Purification and Characterization of Recombinant DiCyp-3

Subcloning into pMAL-c2

Thermal cycling primers were designed to enable cloning of the putative PPIase domain plus the C-terminal extension (272 amino acids) of DiCyp-3 into the plasmid pMal-c2 to generate a fusion protein with maltose-binding protein (MBP). The sequences of the sense primer (5'-ATGG ACCCTGTAACACATCAGAAAGCAGCT-3' (SEQ ID NO:14)) and antisense primer (5'-CGCAAGCTTACCAAGTTGAGAAATCACC AAAAATCTG-3' (SEQ ID NO:15)) corresponded to the codon sequences for aa 256 to 265 and the last 9 aa (aa 519–527) and a stop codon of DiCyp-3, respectively. PCR was performed using Deep Vent DNA polymerase on 1 µg of template pUC19 DNA at 95° C./1 min., 50°C./1 min., 72° C./2 min. for 10 cycles followed by 72° C. for 5 min. The PCR product was run on a 1% low melt-point agarose gel, excised and digested for 30 min with 2U of B-agarase (New England Biolabs, Beverly, Mass.). The supernatant was phenol extracted and ethanol precipitated, and then resuspended in distilled water.

Ligation and transformation reactions were essentially carried out as described in the New England Biolabs Protein Fusion and Purification System Instruction manual. Ligation was performed overnight at 16° C. with 4000 U T4 DNA ligase (New England Biolabs, Beverly, Mass.). The ligation mix was added to 50 µl of competant cells (ER 2267), and incubated on ice for 30 min, heated to 42° C. for 2 min, mixed with 900 µl of LB at 37° C. for 1 hour, and then plated out on LB/amp plates and allowed to grow overnight.

Positive transformants were streaked onto an LB/amp plate with 80 µg/ml X-GAL and 0.1M isopropyl β-D-thiogalacto-pyranoside (IPTG, Sigma Chemical Co., St. Louis, Mo.).) for selection of white colonies. Miniprep DNA was prepared from the positive colonies using the Qiagen (Studio City, Calif.) miniprep system, following the manufacturers' recommendations.

Production and Purification of MBP/DiCyp-3

A single colony was picked and grown overnight at 37° C. in 20 ml of LB amp and this was transferred to 2 L of prewarmed rich broth plus amp. The bacterial cells (strain ER2267) were grown at 37° C. to log phase (OD 600=0.8) and induced with 0.3 mM IPTG at 25° C.–30° C. for 2 hours. Following centrifugation at 5000× g, the cells were resuspended in 200 ml column buffer (20 mM TrisHCl, 200 mM NaCl, 1 mM EDTA) pH 7.4 and frozen overnight at −20° C. The suspension was thawed in cold water, sonicated for 1 minute each time until the suspension became clear. The sonicate was then centrifuged at 30000× g and the supernatant was loaded onto a 2.5×15 cm amylose column which had been equilibrated with 10 volumes of column buffer. The column was washed with 8 volumes of regular column buffer and 2 volumes of column buffer containing 0.5M NaCl. MBP/Cyp-3 was eluted with column buffer plus 10 mM maltose. This procedure yielded 5–15 mg of fusion protein/L.

Cleavage of MBP from the fusion protein was achieved following incubation in 10% Factor Xa (w/w) at 37° C. for 12 hours. Cyp-3 was separated from MBP using a Q-sepharose anion exchange resin (Pharmacia, Piscataway, N.J.).

FIG. 5 illustrates the expression and purification of Cyp-3. Fusion protein is purified using an amylose column (lane B), fusion protein is cleared using Factor Xa protease (lane C) and is purified using a Q-sepharose anion exchange resin (lane D).

PPIase Activity

The PPIase activity of recombinant DiCyp-3 was determined using the standard assay of Fischer, et al., *Nature*, 337:476–478 (1989), with the substrate solvent modifications described by Kofron, et al., *Biochem.*, 30:6127–6134 (1991). The assay measures the ability of DiCyp-3 to convert a proline-containing synthetic peptide from cis to trans. The synthetic peptide is susceptible to chymotrypsin proteolysis only when in the trans configuration, and cleavage results in the release of a measurable chromogenic dye.

The characteristics of recombinant Cyp-3 were examined as a MBP fusion protein and in the purified form (minus MBP). Reactions were performed at 9.5° C. and monitored at 0.3 sec intervals at 400 nm using a Beckman DU 640 spectrophotometer. Pseudo-first-order rate kinetics were calculated using the formula: $k_{obs}=(k_{cat}/K_m)[E]$. Both the fusion protein and purified protein were found to possess PPIase activity with $k_{cat}/K_m$ values of 428±50 and 392±42 mM$^{-1}$s$^{-1}$ respectively. Similar levels of enzyme activity were observed when shorter (beginning at amino acid 263 or 266) or larger fusion constructs (containing both N- and C-terminal extensions) were analyzed in a similar manner. However, a construct corresponding to the enzyme domain alone (amino acid 263–435) was not active as a fusion protein or in a purified form, suggesting that at least part of the C-terminal extension is required for PPIase activity.

Inhibition of PPIase Activity Using CsA

Previous studies have shown that filarial parasites possess a CsA-insensitive 'histidine-containing' (Cyp-1) (Page, et al., *Biochemistry*, supra) and CsA-sensitive 'tryptophan-containing' (Cyp-2) (Ma, et al., *Mol. Biochem. Parasitol.*, supra) cyclophilin with concentrations of 860 nM and 9.3 nM required to inhibit 50% (IC$_{50}$) of their PPIase activity, respectively (FIG. 6). Similar experiments were performed using Cyp-3 fusion protein or purified protein. Recombinant enzyme (15 nM) was preincubated with varying concentrations of CsA (≦5 µM for Cyp-3 and ≦100 µM for MBP-Cyp-3, respectively) at 4° C. for 1 hour before the assays were performed as described above. At the highest concentrations of CsA tested, 5 µM for Cyp-3 and 100 ,M for MBP-Cyp-3, we were unable to detect any inhibition of enzyme activity. Cyp-3 ('tyrosine-containing') is therefore considerably more resistant to CsA inhibition than Cyp-1 ('histidine-containing') or Cyp-2 ('tryptophan-containing') and represents the most CsA-insensitive parasite cyclophilin described to date (FIG. 6). On the basis of these observations it is likely that the C. elegans Cyp-4 (Page, et al., *Biochem. J.* supra) and human Cyp-60 (Wang, et al., *Biochem.*, supra) would be similarly insensitive to inhibition with CsA.

Substrate Specificity Toward Various Peptide Substrates

Since it has been suggested that the reduced sensitivity of certain cyclophilins to CsA may reflect an altered specificity for the putative natural ligands (Kieffer, et al., *J. Biol. Chem.*, 268:12303–12310 (1993)), we compared the ability of purified Cyp-1 ('histidine-containing') (Page, et al., *Biochemistry*, supra), Cyp-2 ('tryptophan-containing') (Ma, et al., *Mol. Biochem. Parasitol*, supra) and Cyp-3 ('tyrosine-containing') proteins to catalyze the isomerization to the trans form of 11 different synthetic peptides of the general structure N-succinyl-Ala-Xaa-cis-Pro-Phe-p-nitroanilide, where Xaa is any of the 11 amino acids listed in FIG. 7. The tripeptide substrate Suc-Phe-Pro-Phe-pNA was also included in the analysis. The catalytic efficiency ($k_{cat}/K_m$) of the substrates varied and a distinct profile emerged for each cyclophilin. Both Cyp-1 ('histidine-containing') and Cyp-2 ('tryptophan-containing') demonstrated a strong preference for the short chain residue alanine (Ala) found in the standard substrate. However only Cyp-2 demonstrated a preference for the negatively charged glutamate (Glu) residue. In total contrast, Cyp-3 was found to favor the straight chain, aliphatic, hydrophobic amino acid norleucine (Nle). These data suggest that the various isoforms may be involved in the folding of different proteins in vivo.

What is claimed is:

1. An isolated and purified cyclophilin endogenous to the parasites *Onchocerca volvulus, Brugia malayi,* and *Dirofilaria immitis,* wherein said cyclophilin includes a tyrosine residue in the drug-binding site.

2. The *Dirofiliaria immitis* cyclophilin of claim 1 having the amino acid sequence set forth in the Sequence Listing as SEQ ID NO:2.

3. A fusion protein comprising the cyclophilin of claim 2 and a binding protein.

4. The fusion protein of claim 3, wherein the binding protein is a sugar binding protein.

5. The fusion protein of claim 4, wherein the sugar binding protein is maltose binding protein.

* * * * *

UNITED STATES PATENT AND TRADEMARK OFFICE
CERTIFICATE OF CORRECTION

PATENT NO. : 6,150,501
DATED : November 21, 2000
INVENTOR(S) : Clotilde K.S. Carlow, Xiqiang Hong and Dong Ma It is certified that error appears in the above-identified patent and that said Letters Patent is hereby corrected as shown below:

Column 1,
Line 1, before "Tyrosine-Containing" insert -- Novel --
Line 36, replace "66:23204-23214" with -- 66:799-806 --
Line 42, replace "Anderson, .et" with -- Anderson, et --

Column 2,
Line 30, replace "(1989) ." with -- (1989) ) . --
Line 32, replace "(1993)" with -- (1993) ) --
Line 44, replace "(1992)," with -- (1992) ), --
Line 64, replace "(1996)." with -- (1996) ). --

Column 5,
Line 48, replace "an" with -- a --
Line 61, replace "target" with -- targets --

Column 7,
Line 1, replace "a" with -- an --

Column 8,
Line 29, replace "112:3431-338" with --112:3431-3438 --
Line 51, after "but" insert -- are --

Column 9,
Line 37, replace "(1983), ." with -- (1983) . --

Column 11,
Line 11, replace "analysis" with -- analysis, --

UNITED STATES PATENT AND TRADEMARK OFFICE
CERTIFICATE OF CORRECTION

PATENT NO. : 6,150,501
DATED : November 21, 2000
INVENTOR(S) : Clotilde K.S. Carlow, Xiqiang Hong and Dong Ma It is certified that error appears in the above-identified patent and that said Letters Patent is hereby corrected as shown below:

Column 11,
Line 35, replace "was" with -- were --
Line 42-43 replace
"CAGAATTCGGCGCGCCTGCAGGTTTAATTACCCAAGTTTGAG" with --
CAGAATTCGGCGCGCCTGCAGGTTTAATTACCCAAGTTTGAG --

Column 13,
Line 38, replace "Louis, Mo.) .)" with -- Louis, Mo.) --
Line 41, replace "facturers' " with -- facturer's --

Column 14,
Line 18, replace "a" with -- an --
Line 48, replace ",M" with -- µM --

Signed and Sealed this

Twenty-fifth Day of September, 2001

Attest:

NICHOLAS P. GODICI
Attesting Officer  Acting Director of the United States Patent and Trademark Office